(12) United States Patent
Chen et al.

(10) Patent No.: US 8,178,358 B2
(45) Date of Patent: May 15, 2012

(54) SERPINE2 AS A BIOMARKER FOR IGA NEPHROPATHY

(75) Inventors: Ann Chen, Taipei (TW); Shuk-Man Ka, Taipei (TW)

(73) Assignee: National Defense Medical Center, Taipei (TW)

( * ) Notice: Subject to any disclaimer, the term of this patent is extended or adjusted under 35 U.S.C. 154(b) by 0 days.

(21) Appl. No.: 12/695,907

(22) Filed: Jan. 28, 2010

(65) Prior Publication Data
US 2011/0183349 A1 Jul. 28, 2011

(51) Int. Cl.
*G01N 33/564* (2006.01)
*G01N 33/53* (2006.01)
*G01N 33/535* (2006.01)
*G01N 33/563* (2006.01)
*C12Q 1/00* (2006.01)
*C12Q 1/25* (2006.01)
*C12Q 1/68* (2006.01)

(52) U.S. Cl. .......... 436/506; 435/4; 435/7.92; 435/6.11; 435/6.12; 424/9.1; 436/512

(58) Field of Classification Search .................. None
See application file for complete search history.

(56) References Cited

U.S. PATENT DOCUMENTS 6,753,164 B2 * 6/2004 Ni et al. ................. 435/69.1

OTHER PUBLICATIONS

Taneda et al., J Am Soc Nephrol. 2008; 19: 243-251.*
Website downloaded from medline on Jun. 22, 2011: nlm.nih.gov/medlineplus/ency/article/000466.htm.; 3 pages total.*
Goto et al., Nephrol Dial Transplant, 2009; 24: 3068-3074.*
Moll et al., Kidney International, 1996; 50: 1936-1945.*
D'Amico, G, Q J Med. 1987, 64: 709-27.*
Hotta et al., Renal Failure, 1998; 20: 413-418.*
Inagi et al., Nephrol Dial Transplant, 2007; 22: 3311-3317.*
Wikström et al., Am J Obstet Gynecol, 2009; 201: 597e1-8.*
Frank Strutz et al., "Identification and Characterization of a Fibroblast Marker: FSP1 F", J. Cell Biol., 130(2):393-405 (Jul. 1995).
LA van Es et al., "GMP-17-positive T-lymphocytes in renal tubules predict progression in early stages of IgA nephropathy", Kidney Int., 73:1426-1433 (2008).
D.D. Torres et al., "The ratio of epidermal growth factor to monocyte chemotactic peptide-1 in the urine predicts renal prognosis in IgA nephropathy ", Kidney Int., 73:327-333 (2008).
Hanlu Ding et al., "Urinary neutrophil gelatinase-associated lipocalin (NGAL) is an early biomarker for renal tubulointerstitial injury in IgA nephropathy", Clinical Immunology, 123:227-234 (2007).
Masaaki Eiro et al., "The Product of Duration and Amount of Proteinuria (Proteinuria Index) Is a Possible Marker for Glomerular and Tubulointerstitial Damage in IgA Nephropathy," Nephron, 90:432-441 (2002).
Bruce A. Julian et al., "Urinary biomarkers of IgA nephropathy and other IgA-associated renal diseases", World J. Urol., 25:467-476 (2007).
Mi-Ra Park et al., "Establishment of a 2-D human urinary proteomic map in IgA nephropathy," Proteomics, 6: 1066-1076 (2006).

\* cited by examiner

*Primary Examiner* — Jeffrey Stucker
*Assistant Examiner* — Christina Borgeest
(74) *Attorney, Agent, or Firm* — Ditthavong Mori & Steiner, P.C.

(57) ABSTRACT

The present invention provides a method for diagnosis or prognosis of IgA nephropathy in a subject based on detection of the expression level of one or more biomarker genes selected from the group consisting of thymosin β4 (Tmsb4), serine or cysteine proteinase inhibitor clade E member 2 (Serpine2), secreted phosphoprotein 1 (OPN), butyrophilin-like-2 (BTNL2), S100 calcium binding protein A8 (S100A8), Cystatin C (CysC), and any combination thereof.

5 Claims, 28 Drawing Sheets

B

C

F

G

B

C

B

C

D

E

A

B

C

D

E

```
                            SEQUENCE LISTING

<160> NUMBER OF SEQ ID NOS: 50

<210> SEQ ID NO 1
<211> LENGTH: 657
<212> TYPE: DNA
<213> ORGANISM: Homo sapiens
<220> FEATURE:
<221> NAME/KEY: CDS
<222> LOCATION: (79)..(213)

<400> SEQUENCE: 1
gacaactcgg tggtggccac tgcgcagacc agacttcgct cgtactcgtg cgcctcgctt        60
cgcttttcct ccgcaacc atg tct gac aaa ccc gat atg gct gag atc gag          111
                    Met Ser Asp Lys Pro Asp Met Ala Glu Ile Glu
                    1               5                  10 aaa ttc gat aag tcg aaa ctg aag aag aca gag acg caa gag aaa aat         159
Lys Phe Asp Lys Ser Lys Leu Lys Lys Thr Glu Thr Gln Glu Lys Asn
                15                  20                  25 cca ctg cct tcc aaa gaa acg att gaa cag gag aag caa gca ggc gaa         207
Pro Leu Pro Ser Lys Glu Thr Ile Glu Gln Glu Lys Gln Ala Gly Glu
        30                  35                  40 tcg taa tgaggcgtgc gccgccaata tgcactgtac attccacaag cattgccttc          263
Ser ttattttact tcttttagct gtttaacttt gtaagatgca aagaggttgg atcaagttta        323
aatgactgtg ctgcccttt cacatcaaag aactactgac aacgaaggcc gcgcctgcct        383
```

```
ttcccatctg tctatctatc tggctggcag ggaaggaaag aacttgcatg ttggtgaagg      443
aagaagtggg gtggaagaag tggggtggga cgacagtgaa atctagagta aaaccaagct      503
ggcccaaggt gtcctgcagg ctgtaatgca gtttaatcag agtgccattt tttttttgt       563 tcaaatgatt ttaattattg gaatgcacaa ttttttttaat atgcaaataa aaagtttaaa    623
aacttaaaaa aaaaaaaaaa aaaaaaaaaa aaaa                                  657
```

```
<210> SEQ ID NO 2
<211> LENGTH: 44
<212> TYPE: PRT
<213> ORGANISM: Homo sapiens

<400> SEQUENCE: 2

Met Ser Asp Lys Pro Asp Met Ala Glu Ile Glu Lys Phe Asp Lys Ser
1               5                   10                  15
Lys Leu Lys Lys Thr Glu Thr Gln Glu Lys Asn Pro Leu Pro Ser Lys
                20                  25                  30
Glu Thr Ile Glu Gln Glu Lys Gln Ala Gly Glu Ser
            35                  40

<210> SEQ ID NO 3
<211> LENGTH: 1230
<212> TYPE: DNA
<213> ORGANISM: Homo sapiens
<220> FEATURE:
<221> NAME/KEY: CDS
<222> LOCATION: (1)..(1230)

<400> SEQUENCE: 3
```

```
atg agt gac tgc agg tcg tcc ttg gtg gaa gga acc atg aac tgg cat       48
Met Ser Asp Cys Arg Ser Ser Leu Val Glu Gly Thr Met Asn Trp His
1               5                   10                  15 ctc ccc ctc ttc ctc ttg gcc tct gtg acg ctg cct tcc atc tgc tcc       96
Leu Pro Leu Phe Leu Leu Ala Ser Val Thr Leu Pro Ser Ile Cys Ser
                20                  25                  30 cac ttc aat cct ctg tct ctc gag gaa cta ggc tcc aac acg ggg atc      144
His Phe Asn Pro Leu Ser Leu Glu Glu Leu Gly Ser Asn Thr Gly Ile
            35                  40                  45 cag gtt ttc aat cag att gtg aag tcg agg cct cat gac aac atc gtg      192
Gln Val Phe Asn Gln Ile Val Lys Ser Arg Pro His Asp Asn Ile Val
50                  55                  60 atc tct ccc cat ggg att gcg tcg gtc ctg ggg atg ctt cag ctg ggg      240
Ile Ser Pro His Gly Ile Ala Ser Val Leu Gly Met Leu Gln Leu Gly
65                  70                  75                  80 gcg gac ggc agg acc aag aag cag ctc gcc atg gtg atg aga tac ggc      288
Ala Asp Gly Arg Thr Lys Lys Gln Leu Ala Met Val Met Arg Tyr Gly
                85                  90                  95 gta aat gga gtt ggt aaa ata tta aag aag atc aac aag gcc atc gtc      336
Val Asn Gly Val Gly Lys Ile Leu Lys Lys Ile Asn Lys Ala Ile Val
                100                 105                 110 tcc aag aag aat aaa gac att gtg aca gtg gct aac gcc gtg ttt gtt      384
Ser Lys Lys Asn Lys Asp Ile Val Thr Val Ala Asn Ala Val Phe Val
            115                 120                 125 aag aat gcc tct gaa att gaa gtg cct ttt gtt aca agg aac aaa gat      432
Lys Asn Ala Ser Glu Ile Glu Val Pro Phe Val Thr Arg Asn Lys Asp
130                 135                 140 gtg ttc cag tgt gag gtc cgg aat gtg aac ttt gag gat cca gcc tct      480
Val Phe Gln Cys Glu Val Arg Asn Val Asn Phe Glu Asp Pro Ala Ser
145                 150                 155                 160 gcc tgt gat tcc atc aat gca tgg gtt aaa aat gaa acc agg gat atg      528
```

```
Ala Cys Asp Ser Ile Asn Ala Trp Val Lys Asn Glu Thr Arg Asp Met
                165                 170                 175 att gac aat ctg ctg tcc cca gat ctt att gat ggt gtg ctc acc aga    576
Ile Asp Asn Leu Leu Ser Pro Asp Leu Ile Asp Gly Val Leu Thr Arg
            180                 185                 190 ctg gtc ctc gtc aac gca gtg tat ttc aag ggt ctg tgg aaa tca cgg    624
Leu Val Leu Val Asn Ala Val Tyr Phe Lys Gly Leu Trp Lys Ser Arg
        195                 200                 205 ttc caa ccc gag aac aca aag aaa cgc act ttc gtg gca gcc gac ggg    672
Phe Gln Pro Glu Asn Thr Lys Lys Arg Thr Phe Val Ala Ala Asp Gly
    210                 215                 220 aaa tcc tat caa gtg cca atg ctg gcc cag ctc tcc gtg ttc cgg tgt    720
Lys Ser Tyr Gln Val Pro Met Leu Ala Gln Leu Ser Val Phe Arg Cys
225                 230                 235                 240 ggg tcg aca agt gcc ccc aat gat tta tgg tac aac ttc att gaa ctg    768
Gly Ser Thr Ser Ala Pro Asn Asp Leu Trp Tyr Asn Phe Ile Glu Leu
                245                 250                 255 ccc tac cac ggg gaa agc atc agc atg ctg att gca ctg ccg act gag    816
Pro Tyr His Gly Glu Ser Ile Ser Met Leu Ile Ala Leu Pro Thr Glu
            260                 265                 270 agc tcc act ccg ctg tct gcc atc atc cca cac atc agc acc aag acc    864
Ser Ser Thr Pro Leu Ser Ala Ile Ile Pro His Ile Ser Thr Lys Thr
        275                 280                 285 ata gac agc tgg atg agc atc atg gtg ccc aag agg gtg cag gtg atc    912
Ile Asp Ser Trp Met Ser Ile Met Val Pro Lys Arg Val Gln Val Ile
    290                 295                 300 ctg ccc aag ttc aca gct gta gca caa aca gat ttg aag gag ccg ctg    960
Leu Pro Lys Phe Thr Ala Val Ala Gln Thr Asp Leu Lys Glu Pro Leu
305                 310                 315                 320 aaa gtt ctt ggc att act gac atg ttt gat tca tca aag gca aat ttt   1008
Lys Val Leu Gly Ile Thr Asp Met Phe Asp Ser Ser Lys Ala Asn Phe
                325                 330                 335 gca aaa ata aca agg tca gaa aac ctc cat gtt tct cat atc ttg caa   1056
Ala Lys Ile Thr Arg Ser Glu Asn Leu His Val Ser His Ile Leu Gln
            340                 345                 350 aaa gca aaa att gaa gtc agt gaa gat gga acc aaa gct tca gca gca   1104
Lys Ala Lys Ile Glu Val Ser Glu Asp Gly Thr Lys Ala Ser Ala Ala
        355                 360                 365 aca act gca att ctc att gca aga tca tcg cct ccc tgg ttt ata gta   1152
Thr Thr Ala Ile Leu Ile Ala Arg Ser Ser Pro Pro Trp Phe Ile Val
    370                 375                 380 gac aga cct ttt ctg ttt ttc atc cga cat aat cct aca ggt gct gtg   1200
Asp Arg Pro Phe Leu Phe Phe Ile Arg His Asn Pro Thr Gly Ala Val
385                 390                 395                 400 tta ttc atg ggg cag ata aac aaa ccc tga                           1230
Leu Phe Met Gly Gln Ile Asn Lys Pro
                405

<210> SEQ ID NO 4
<211> LENGTH: 409
<212> TYPE: PRT
<213> ORGANISM: Homo sapiens

<400> SEQUENCE: 4

Met Ser Asp Cys Arg Ser Ser Leu Val Glu Gly Thr Met Asn Trp His
1               5                   10                  15

Leu Pro Leu Phe Leu Leu Ala Ser Val Thr Leu Pro Ser Ile Cys Ser
                20                  25                  30

His Phe Asn Pro Leu Ser Leu Glu Glu Leu Gly Ser Asn Thr Gly Ile
            35                  40                  45
```

```
Gln Val Phe Asn Gln Ile Val Lys Ser Arg Pro His Asp Asn Ile Val
 50                  55                  60
Ile Ser Pro His Gly Ile Ala Ser Val Leu Gly Met Leu Gln Leu Gly
 65                  70                  75                  80
Ala Asp Gly Arg Thr Lys Lys Gln Leu Ala Met Val Met Arg Tyr Gly
                 85                  90                  95
Val Asn Gly Val Gly Lys Ile Leu Lys Lys Ile Asn Lys Ala Ile Val
                100                 105                 110
Ser Lys Lys Asn Lys Asp Ile Val Thr Val Ala Asn Ala Val Phe Val
                115                 120                 125
Lys Asn Ala Ser Glu Ile Glu Val Pro Phe Val Thr Arg Asn Lys Asp
130                 135                 140
Val Phe Gln Cys Glu Val Arg Asn Val Asn Phe Glu Asp Pro Ala Ser
145                 150                 155                 160
Ala Cys Asp Ser Ile Asn Ala Trp Val Lys Asn Glu Thr Arg Asp Met
                165                 170                 175
Ile Asp Asn Leu Leu Ser Pro Asp Leu Ile Asp Gly Val Leu Thr Arg
                180                 185                 190
Leu Val Leu Val Asn Ala Val Tyr Phe Lys Gly Leu Trp Lys Ser Arg
                195                 200                 205
Phe Gln Pro Glu Asn Thr Lys Lys Arg Thr Phe Val Ala Ala Asp Gly
210                 215                 220
Lys Ser Tyr Gln Val Pro Met Leu Ala Gln Leu Ser Val Phe Arg Cys
225                 230                 235                 240
Gly Ser Thr Ser Ala Pro Asn Asp Leu Trp Tyr Asn Phe Ile Glu Leu
                245                 250                 255
Pro Tyr His Gly Glu Ser Ile Ser Met Leu Ile Ala Leu Pro Thr Glu
                260                 265                 270
Ser Ser Thr Pro Leu Ser Ala Ile Ile Pro His Ile Ser Thr Lys Thr
                275                 280                 285
Ile Asp Ser Trp Met Ser Ile Met Val Pro Lys Arg Val Gln Val Ile
                290                 295                 300
Leu Pro Lys Phe Thr Ala Val Ala Gln Thr Asp Leu Lys Glu Pro Leu
305                 310                 315                 320
Lys Val Leu Gly Ile Thr Asp Met Phe Asp Ser Ser Lys Ala Asn Phe
                325                 330                 335
Ala Lys Ile Thr Arg Ser Glu Asn Leu His Val Ser His Ile Leu Gln
                340                 345                 350
Lys Ala Lys Ile Glu Val Ser Glu Asp Gly Thr Lys Ala Ser Ala Ala
                355                 360                 365
Thr Thr Ala Ile Leu Ile Ala Arg Ser Ser Pro Pro Trp Phe Ile Val
370                 375                 380
Asp Arg Pro Phe Leu Phe Phe Ile Arg His Asn Pro Thr Gly Ala Val
385                 390                 395                 400
Leu Phe Met Gly Gln Ile Asn Lys Pro
                405

<210> SEQ ID NO 5
<211> LENGTH: 903
<212> TYPE: DNA
<213> ORGANISM: Homo sapiens
<220> FEATURE:
<221> NAME/KEY: CDS
<222> LOCATION: (1)..(903)

<400> SEQUENCE: 5
```

```
atg aga att gca gtg att tgc ttt tgc ctc cta ggc atc acc tgt gcc    48
Met Arg Ile Ala Val Ile Cys Phe Cys Leu Leu Gly Ile Thr Cys Ala
 1               5                  10                  15 ata cca gtt aaa cag gct gat tct gga agt tct gag gaa aag cag ctt    96
Ile Pro Val Lys Gln Ala Asp Ser Gly Ser Ser Glu Glu Lys Gln Leu
             20                  25                  30 tac aac aaa tac cca gat gct gtg gcc aca tgg cta aac cct gac cca   144
Tyr Asn Lys Tyr Pro Asp Ala Val Ala Thr Trp Leu Asn Pro Asp Pro
         35                  40                  45 tct cag aag cag aat ctc cta gcc cca cag acc ctt cca agt aag tcc   192
Ser Gln Lys Gln Asn Leu Leu Ala Pro Gln Thr Leu Pro Ser Lys Ser
     50                  55                  60 aac gaa agc cat gac cac atg gat gat atg gat gat gaa gat gat gat   240
Asn Glu Ser His Asp His Met Asp Asp Met Asp Asp Glu Asp Asp Asp
65                  70                  75                  80 gac cat gtg gac agc cag gac tcc att gac tcg aac gac tct gat gat   288
Asp His Val Asp Ser Gln Asp Ser Ile Asp Ser Asn Asp Ser Asp Asp
                 85                  90                  95 gta gat gac act gat gat tct cac cag tct gat gag tct cac cat tct   336
Val Asp Asp Thr Asp Asp Ser His Gln Ser Asp Glu Ser His His Ser
            100                 105                 110 gat gaa tct gat gaa ctg gtc act gat ttt ccc acg gac ctg cca gca   384
Asp Glu Ser Asp Glu Leu Val Thr Asp Phe Pro Thr Asp Leu Pro Ala
        115                 120                 125 acc gaa gtt ttc act cca gtt gtc ccc aca gta gac aca tat gat ggc   432
Thr Glu Val Phe Thr Pro Val Val Pro Thr Val Asp Thr Tyr Asp Gly
    130                 135                 140 cga ggt gat agt gtg gtt tat gga ctg agg tca aaa tct aag aag ttt   480
Arg Gly Asp Ser Val Val Tyr Gly Leu Arg Ser Lys Ser Lys Lys Phe
145                 150                 155                 160 cgc aga cct gac atc cag tac cct gat gct aca gac gag gac atc acc   528
Arg Arg Pro Asp Ile Gln Tyr Pro Asp Ala Thr Asp Glu Asp Ile Thr
                165                 170                 175 tca cac atg gaa agc gag gag ttg aat ggt gca tac aag gcc atc ccc   576
Ser His Met Glu Ser Glu Glu Leu Asn Gly Ala Tyr Lys Ala Ile Pro
            180                 185                 190 gtt gcc cag gac ctg aac gcg cct tct gat tgg gac agc cgt ggg aag   624
Val Ala Gln Asp Leu Asn Ala Pro Ser Asp Trp Asp Ser Arg Gly Lys
        195                 200                 205 gac agt tat gaa acg agt cag ctg gat gac cag agt gct gaa acc cac   672
Asp Ser Tyr Glu Thr Ser Gln Leu Asp Asp Gln Ser Ala Glu Thr His
    210                 215                 220 agc cac aag cag tcc aga tta tat aag cgg aaa gcc aat gat gag agc   720
Ser His Lys Gln Ser Arg Leu Tyr Lys Arg Lys Ala Asn Asp Glu Ser
225                 230                 235                 240 aat gag cat tcc gat gtg att gat agt cag gaa ctt tcc aaa gtc agc   768
Asn Glu His Ser Asp Val Ile Asp Ser Gln Glu Leu Ser Lys Val Ser
                245                 250                 255 cgt gaa ttc cac agc cat gaa ttt cac agc cat gaa gat atg ctg gtt   816
Arg Glu Phe His Ser His Glu Phe His Ser His Glu Asp Met Leu Val
            260                 265                 270 gta gac ccc aaa agt aag gaa gaa gat aaa cac ctg aaa ttt cgt att   864
Val Asp Pro Lys Ser Lys Glu Glu Asp Lys His Leu Lys Phe Arg Ile
        275                 280                 285 tct cat gaa tta gat agt gca tct tct gag gtc aat taa                903
Ser His Glu Leu Asp Ser Ala Ser Ser Glu Val Asn
    290                 295                 300

<210> SEQ ID NO 6
<211> LENGTH: 300
<212> TYPE: PRT
```

<213> ORGANISM: Homo sapiens

<400> SEQUENCE: 6

```
Met Arg Ile Ala Val Ile Cys Phe Cys Leu Leu Gly Ile Thr Cys Ala
1               5                   10                  15
Ile Pro Val Lys Gln Ala Asp Ser Gly Ser Ser Glu Glu Lys Gln Leu
            20                  25                  30
Tyr Asn Lys Tyr Pro Asp Ala Val Ala Thr Trp Leu Asn Pro Asp Pro
        35                  40                  45
Ser Gln Lys Gln Asn Leu Leu Ala Pro Gln Thr Leu Pro Ser Lys Ser
    50                  55                  60
Asn Glu Ser His Asp His Met Asp Asp Met Asp Asp Glu Asp Asp Asp
65                  70                  75                  80
Asp His Val Asp Ser Gln Asp Ser Ile Asp Ser Asn Asp Ser Asp Asp
                85                  90                  95
Val Asp Asp Thr Asp Asp Ser His Gln Ser Asp Glu Ser His His Ser
            100                 105                 110
Asp Glu Ser Asp Glu Leu Val Thr Asp Phe Pro Thr Asp Leu Pro Ala
        115                 120                 125
Thr Glu Val Phe Thr Pro Val Val Pro Thr Val Asp Thr Tyr Asp Gly
    130                 135                 140
Arg Gly Asp Ser Val Val Tyr Gly Leu Arg Ser Lys Ser Lys Lys Phe
145                 150                 155                 160
Arg Arg Pro Asp Ile Gln Tyr Pro Asp Ala Thr Asp Glu Asp Ile Thr
                165                 170                 175
Ser His Met Glu Ser Glu Glu Leu Asn Gly Ala Tyr Lys Ala Ile Pro
            180                 185                 190
Val Ala Gln Asp Leu Asn Ala Pro Ser Asp Trp Asp Ser Arg Gly Lys
        195                 200                 205
Asp Ser Tyr Glu Thr Ser Gln Leu Asp Asp Gln Ser Ala Glu Thr His
    210                 215                 220
Ser His Lys Gln Ser Arg Leu Tyr Lys Arg Lys Ala Asn Asp Glu Ser
225                 230                 235                 240
Asn Glu His Ser Asp Val Ile Asp Ser Gln Glu Leu Ser Lys Val Ser
                245                 250                 255
Arg Glu Phe His Ser His Glu Phe His Ser His Glu Asp Met Leu Val
            260                 265                 270
Val Asp Pro Lys Ser Lys Glu Glu Asp Lys His Leu Lys Phe Arg Ile
        275                 280                 285
Ser His Glu Leu Asp Ser Ala Ser Ser Glu Val Asn
    290                 295                 300
```

<210> SEQ ID NO 7
<211> LENGTH: 1368
<212> TYPE: DNA
<213> ORGANISM: Homo sapiens
<220> FEATURE:
<221> NAME/KEY: CDS
<222> LOCATION: (1)..(1368)

<400> SEQUENCE: 7

```
atg gtg gat ttt cca ggc tac aat ctg tct ggt gca gtc gcc tcc ttc      48
Met Val Asp Phe Pro Gly Tyr Asn Leu Ser Gly Ala Val Ala Ser Phe
1               5                   10                  15 cta ttc atc ctg ctg aca atg aag cag tca gaa gac ttt aga gtc att      96
Leu Phe Ile Leu Leu Thr Met Lys Gln Ser Glu Asp Phe Arg Val Ile
            20                  25                  30
```

```
ggc cct gct cat cct atc ctg gcc ggg gtt ggg gaa gat gcc ctg tta      144
Gly Pro Ala His Pro Ile Leu Ala Gly Val Gly Glu Asp Ala Leu Leu
         35                  40                  45 acc tgc cag cta ctc ccc aag agg acc aca atg cac gtg gag gtg agg      192
Thr Cys Gln Leu Leu Pro Lys Arg Thr Thr Met His Val Glu Val Arg
 50                  55                  60 tgg tac cgc tca gag ccc agc aca cct gtg ttt gtg cac agg gat gga      240
Trp Tyr Arg Ser Glu Pro Ser Thr Pro Val Phe Val His Arg Asp Gly
 65                  70                  75                  80 gtg gag gtg act gag atg cag atg gag gag tac aga ggc tgg gta gag      288
Val Glu Val Thr Glu Met Gln Met Glu Glu Tyr Arg Gly Trp Val Glu
                 85                  90                  95 tgg ata gag aat ggc att gca aag gga aat gtg gca ctg aag ata cac      336
Trp Ile Glu Asn Gly Ile Ala Lys Gly Asn Val Ala Leu Lys Ile His
            100                 105                 110 aac atc cag ccc tcc gac aat gga caa tac tgg tgc cat ttc cag gat      384
Asn Ile Gln Pro Ser Asp Asn Gly Gln Tyr Trp Cys His Phe Gln Asp
        115                 120                 125 ggg aac tac tgt gga gaa aca agc ttg ctg ctc aaa gta gca ggt ctg      432
Gly Asn Tyr Cys Gly Glu Thr Ser Leu Leu Leu Lys Val Ala Gly Leu
130                 135                 140 ggg tct gcc cct agc atc cac atg gag gga cct ggg gag agt gga gtc      480
Gly Ser Ala Pro Ser Ile His Met Glu Gly Pro Gly Glu Ser Gly Val
145                 150                 155                 160 cag ctt gtg tgc act gca agg ggc tgg ttc cca gag ccc cag gtg tat      528
Gln Leu Val Cys Thr Ala Arg Gly Trp Phe Pro Glu Pro Gln Val Tyr
                165                 170                 175 tgg gaa gac atc cgg gga gag aag ctg ctg gcc gtg tct gag cat cgc      576
Trp Glu Asp Ile Arg Gly Glu Lys Leu Leu Ala Val Ser Glu His Arg
            180                 185                 190 atc caa gat aaa gat ggc ctg ttc tat gcg gaa gcc acc ctg gtg gtc      624
Ile Gln Asp Lys Asp Gly Leu Phe Tyr Ala Glu Ala Thr Leu Val Val
        195                 200                 205 agg aac gcc tct gca gag tct gtg tcc tgc ttg gtc cac aac ccc gtc      672
Arg Asn Ala Ser Ala Glu Ser Val Ser Cys Leu Val His Asn Pro Val
210                 215                 220 ctc act gag gag aag ggg tcg gtc atc agc ctc cca gag aaa ctc cag      720
Leu Thr Glu Glu Lys Gly Ser Val Ile Ser Leu Pro Glu Lys Leu Gln
225                 230                 235                 240 act gag ctg gct tct tta aaa gtg aat gga cct tcc cag ccc atc ctc      768
Thr Glu Leu Ala Ser Leu Lys Val Asn Gly Pro Ser Gln Pro Ile Leu
                245                 250                 255 gtc aga gtg gga gaa gat ata cag cta acc tgt tac ctg tcc ccc aag      816
Val Arg Val Gly Glu Asp Ile Gln Leu Thr Cys Tyr Leu Ser Pro Lys
            260                 265                 270 gcg aat gca cag agc atg gag gtg agg tgg gac cga tcc cac cgt tac      864
Ala Asn Ala Gln Ser Met Glu Val Arg Trp Asp Arg Ser His Arg Tyr
        275                 280                 285 cct gct gtg cat gtg tat atg gat ggg gac cat gtg gct gga gag cag      912
Pro Ala Val His Val Tyr Met Asp Gly Asp His Val Ala Gly Glu Gln
290                 295                 300 atg gca gag tac aga ggg agg act gta ctg gtg agt gac gcc att gac      960
Met Ala Glu Tyr Arg Gly Arg Thr Val Leu Val Ser Asp Ala Ile Asp
305                 310                 315                 320 gag ggc aga ctg acc ctg cag ata ctc agt gcc aga cct tcg gac gac     1008
Glu Gly Arg Leu Thr Leu Gln Ile Leu Ser Ala Arg Pro Ser Asp Asp
                325                 330                 335 ggg cag tac cgc tgc ctt ttt gaa aaa gat gat gtc tac cag gag gcc     1056
Gly Gln Tyr Arg Cys Leu Phe Glu Lys Asp Asp Val Tyr Gln Glu Ala
            340                 345                 350
```

```
agt ttg gat ctg aag gtg gta agt ctg ggt tct tcc cca ctg atc act    1104
Ser Leu Asp Leu Lys Val Val Ser Leu Gly Ser Ser Pro Leu Ile Thr
        355                 360                 365 gtg gag ggg caa gaa gat gga gaa atg cag ccg atg tgc tct tca gat    1152
Val Glu Gly Gln Glu Asp Gly Glu Met Gln Pro Met Cys Ser Ser Asp
370                 375                 380 ggg tgg ttc cca cag ccc cac gtg cca tgg agg gac atg gaa gga aag    1200
Gly Trp Phe Pro Gln Pro His Val Pro Trp Arg Asp Met Glu Gly Lys
385                 390                 395                 400 acg ata cca tca tct tcc cag gcc ctg act caa ggc agc cac ggg ctg    1248
Thr Ile Pro Ser Ser Ser Gln Ala Leu Thr Gln Gly Ser His Gly Leu
            405                 410                 415 ttc cac gtg cag aca ttg cta agg gtc aca aac atc tcc gct gtg gac    1296
Phe His Val Gln Thr Leu Leu Arg Val Thr Asn Ile Ser Ala Val Asp
            420                 425                 430 gtc act tgt tcc atc agc atc ccc ttt ttg ggc gag gag aaa atc gca    1344
Val Thr Cys Ser Ile Ser Ile Pro Phe Leu Gly Glu Glu Lys Ile Ala
            435                 440                 445 act ttt tct ctc tca ggt tgg tga                                    1368
Thr Phe Ser Leu Ser Gly Trp
450                 455

<210> SEQ ID NO 8
<211> LENGTH: 455
<212> TYPE: PRT
<213> ORGANISM: Homo sapiens

<400> SEQUENCE: 8

Met Val Asp Phe Pro Gly Tyr Asn Leu Ser Gly Ala Val Ala Ser Phe
1               5                   10                  15

Leu Phe Ile Leu Leu Thr Met Lys Gln Ser Glu Asp Phe Arg Val Ile
            20                  25                  30

Gly Pro Ala His Pro Ile Leu Ala Gly Val Gly Glu Asp Ala Leu Leu
        35                  40                  45

Thr Cys Gln Leu Leu Pro Lys Arg Thr Thr Met His Val Glu Val Arg
    50                  55                  60

Trp Tyr Arg Ser Glu Pro Ser Thr Pro Val Phe Val His Arg Asp Gly
65                  70                  75                  80

Val Glu Val Thr Glu Met Gln Met Glu Glu Tyr Arg Gly Trp Val Glu
                85                  90                  95

Trp Ile Glu Asn Gly Ile Ala Lys Gly Asn Val Ala Leu Lys Ile His
            100                 105                 110

Asn Ile Gln Pro Ser Asp Asn Gly Gln Tyr Trp Cys His Phe Gln Asp
        115                 120                 125

Gly Asn Tyr Cys Gly Glu Thr Ser Leu Leu Lys Val Ala Gly Leu
    130                 135                 140

Gly Ser Ala Pro Ser Ile His Met Glu Gly Pro Gly Glu Ser Gly Val
145                 150                 155                 160

Gln Leu Val Cys Thr Ala Arg Gly Trp Phe Pro Glu Pro Gln Val Tyr
                165                 170                 175

Trp Glu Asp Ile Arg Gly Glu Lys Leu Leu Ala Val Ser Glu His Arg
            180                 185                 190

Ile Gln Asp Lys Asp Gly Leu Phe Tyr Ala Glu Ala Thr Leu Val Val
        195                 200                 205

Arg Asn Ala Ser Ala Glu Ser Val Ser Cys Leu Val His Asn Pro Val
    210                 215                 220

Leu Thr Glu Glu Lys Gly Ser Val Ile Ser Leu Pro Glu Lys Leu Gln
225                 230                 235                 240
```

```
Thr Glu Leu Ala Ser Leu Lys Val Asn Gly Pro Ser Gln Pro Ile Leu
            245                 250                 255

Val Arg Val Gly Glu Asp Ile Gln Leu Thr Cys Tyr Leu Ser Pro Lys
        260                 265                 270

Ala Asn Ala Gln Ser Met Glu Val Arg Trp Asp Arg Ser His Arg Tyr
            275                 280                 285

Pro Ala Val His Val Tyr Met Asp Gly Asp His Val Ala Gly Glu Gln
        290                 295                 300

Met Ala Glu Tyr Arg Gly Arg Thr Val Leu Val Ser Asp Ala Ile Asp
305                 310                 315                 320

Glu Gly Arg Leu Thr Leu Gln Ile Leu Ser Ala Arg Pro Ser Asp Asp
                325                 330                 335

Gly Gln Tyr Arg Cys Leu Phe Glu Lys Asp Asp Val Tyr Gln Glu Ala
            340                 345                 350

Ser Leu Asp Leu Lys Val Val Ser Leu Gly Ser Ser Pro Leu Ile Thr
        355                 360                 365

Val Glu Gly Gln Glu Asp Gly Glu Met Gln Pro Met Cys Ser Ser Asp
    370                 375                 380

Gly Trp Phe Pro Gln Pro His Val Pro Trp Arg Asp Met Glu Gly Lys
385                 390                 395                 400

Thr Ile Pro Ser Ser Gln Ala Leu Thr Gln Gly Ser His Gly Leu
                405                 410                 415

Phe His Val Gln Thr Leu Leu Arg Val Thr Asn Ile Ser Ala Val Asp
            420                 425                 430

Val Thr Cys Ser Ile Ser Ile Pro Phe Leu Gly Glu Glu Lys Ile Ala
        435                 440                 445

Thr Phe Ser Leu Ser Gly Trp
    450                 455

<210> SEQ ID NO 9
<211> LENGTH: 282
<212> TYPE: DNA
<213> ORGANISM: Homo sapiens
<220> FEATURE:
<221> NAME/KEY: CDS
<222> LOCATION: (1)..(282)

<400> SEQUENCE: 9 atg ttg acc gag ctg gag aaa gcc ttg aac tct atc atc gac gtc tac     48
Met Leu Thr Glu Leu Glu Lys Ala Leu Asn Ser Ile Ile Asp Val Tyr
1               5                   10                  15 cac aag tac tcc ctg ata aag ggg aat ttc cat gcc gtc tac agg gat     96
His Lys Tyr Ser Leu Ile Lys Gly Asn Phe His Ala Val Tyr Arg Asp
            20                  25                  30 gac ctg aag aaa ttg cta gag acc gag tgt cct cag tat atc agg aaa    144
Asp Leu Lys Lys Leu Leu Glu Thr Glu Cys Pro Gln Tyr Ile Arg Lys
        35                  40                  45 aag ggt gca gac gtc tgg ttc aaa gag ttg gat atc aac act gat ggt    192
Lys Gly Ala Asp Val Trp Phe Lys Glu Leu Asp Ile Asn Thr Asp Gly
    50                  55                  60 gca gtt aac ttc cag gag ttc ctc att ctg gtg ata aag atg ggc gtg    240
Ala Val Asn Phe Gln Glu Phe Leu Ile Leu Val Ile Lys Met Gly Val
65                  70                  75                  80 gca gcc cac aaa aaa agc cat gaa gaa agc cac aaa gag tag            282
Ala Ala His Lys Lys Ser His Glu Glu Ser His Lys Glu
                85                  90

<210> SEQ ID NO 10
```

<211> LENGTH: 93
<212> TYPE: PRT
<213> ORGANISM: Homo sapiens

<400> SEQUENCE: 10

```
Met Leu Thr Glu Leu Glu Lys Ala Leu Asn Ser Ile Ile Asp Val Tyr
1               5                   10                  15

His Lys Tyr Ser Leu Ile Lys Gly Asn Phe His Ala Val Tyr Arg Asp
            20                  25                  30

Asp Leu Lys Lys Leu Leu Glu Thr Glu Cys Pro Gln Tyr Ile Arg Lys
        35                  40                  45

Lys Gly Ala Asp Val Trp Phe Lys Glu Leu Asp Ile Asn Thr Asp Gly
    50                  55                  60

Ala Val Asn Phe Gln Glu Phe Leu Ile Leu Val Ile Lys Met Gly Val
65                  70                  75                  80

Ala Ala His Lys Lys Ser His Glu Glu Ser His Lys Glu
                85                  90
```

<210> SEQ ID NO 11
<211> LENGTH: 441
<212> TYPE: DNA
<213> ORGANISM: Homo sapiens
<220> FEATURE:
<221> NAME/KEY: CDS
<222> LOCATION: (1)..(441)

<400> SEQUENCE: 11

```
atg gcc ggg ccc ctg cgc gcc ccg ctg ctc ctg ctg gcc atc ctg gcc      48
Met Ala Gly Pro Leu Arg Ala Pro Leu Leu Leu Leu Ala Ile Leu Ala
1               5                   10                  15 gtg gcc ctg gcc gtg agc ccc gcg gcc ggc tcc agt ccc ggc aag ccg      96
Val Ala Leu Ala Val Ser Pro Ala Ala Gly Ser Ser Pro Gly Lys Pro
            20                  25                  30 ccg cgc ctg gtg gga ggc ccc atg gac gcc agc gtg gag gag gag ggt     144
Pro Arg Leu Val Gly Gly Pro Met Asp Ala Ser Val Glu Glu Glu Gly
        35                  40                  45 gtg cgg cgt gca ctg gac ttt gcc gtc ggc gag tac aac aaa gcc agc     192
Val Arg Arg Ala Leu Asp Phe Ala Val Gly Glu Tyr Asn Lys Ala Ser
    50                  55                  60 aac gac atg tac cac agc cgc gcg ctg cag gtg gtg cgc gcc cgc aag     240
Asn Asp Met Tyr His Ser Arg Ala Leu Gln Val Val Arg Ala Arg Lys
65                  70                  75                  80 cag atc gta gct ggg gtg aac tac ttc ttg gac gtg gag ctg ggc cga     288
Gln Ile Val Ala Gly Val Asn Tyr Phe Leu Asp Val Glu Leu Gly Arg
                85                  90                  95 acc acg tgt acc aag acc cag ccc aac ttg gac aac tgc ccc ttc cat     336
Thr Thr Cys Thr Lys Thr Gln Pro Asn Leu Asp Asn Cys Pro Phe His
            100                 105                 110 gac cag cca cat ctg aaa agg aaa gca ttc tgc tct ttc cag atc tac     384
Asp Gln Pro His Leu Lys Arg Lys Ala Phe Cys Ser Phe Gln Ile Tyr
        115                 120                 125 gct gtg cct tgg cag ggc aca atg acc ttg tcg aaa tcc acc tgt cag     432
Ala Val Pro Trp Gln Gly Thr Met Thr Leu Ser Lys Ser Thr Cys Gln
    130                 135                 140 gac gcc tag                                                          441
Asp Ala
145
```

<210> SEQ ID NO 12
<211> LENGTH: 146
<212> TYPE: PRT
<213> ORGANISM: Homo sapiens

<400> SEQUENCE: 12

Met Ala Gly Pro Leu Arg Ala Pro Leu Leu Leu Ala Ile Leu Ala
1               5                   10                  15

Val Ala Leu Ala Val Ser Pro Ala Gly Ser Ser Pro Gly Lys Pro
            20                  25                  30

Pro Arg Leu Val Gly Gly Pro Met Asp Ala Ser Val Glu Glu Gly
        35                  40                  45

Val Arg Arg Ala Leu Asp Phe Ala Val Gly Glu Tyr Asn Lys Ala Ser
    50                  55                  60

Asn Asp Met Tyr His Ser Arg Ala Leu Gln Val Val Arg Ala Arg Lys
65                  70                  75                  80

Gln Ile Val Ala Gly Val Asn Tyr Phe Leu Asp Val Glu Leu Gly Arg
                85                  90                  95

Thr Thr Cys Thr Lys Thr Gln Pro Asn Leu Asp Asn Cys Pro Phe His
            100                 105                 110

Asp Gln Pro His Leu Lys Arg Lys Ala Phe Cys Ser Phe Gln Ile Tyr
            115                 120                 125

Ala Val Pro Trp Gln Gly Thr Met Thr Leu Ser Lys Ser Thr Cys Gln
130                 135                 140

Asp Ala
145

<210> SEQ ID NO 13
<211> LENGTH: 19
<212> TYPE: DNA
<213> ORGANISM: Artificial Sequence
<220> FEATURE:
<223> OTHER INFORMATION: moise primer_BTNL2f

<400> SEQUENCE: 13
ctctgggcca ggagaaaac                                            19

<210> SEQ ID NO 14
<211> LENGTH: 21
<212> TYPE: DNA
<213> ORGANISM: Artificial Sequence
<220> FEATURE:
<223> OTHER INFORMATION: mouse primer_BTNL2r

<400> SEQUENCE: 14
tgagcctctc atcagaagga a                                         21

<210> SEQ ID NO 15
<211> LENGTH: 20
<212> TYPE: DNA
<213> ORGANISM: Artificial Sequence
<220> FEATURE:
<223> OTHER INFORMATION: mouse primer_CysCf

<400> SEQUENCE: 15
tacaacaagg gcagcaacga                                           20

<210> SEQ ID NO 16
<211> LENGTH: 20
<212> TYPE: DNA
<213> ORGANISM: Artificial Sequence
<220> FEATURE:
<223> OTHER INFORMATION: mouse primer_CysCr

<400> SEQUENCE: 16
gcacccttct gcgagatgaa                                           20

<210> SEQ ID NO 17
<211> LENGTH: 19
<212> TYPE: DNA
<213> ORGANISM: Artificial Sequence
<220> FEATURE:
<223> OTHER INFORMATION: mouse primer_GAPDHf

<400> SEQUENCE: 17
tccgcccctt ctgccgatg                                              19

<210> SEQ ID NO 18
<211> LENGTH: 21
<212> TYPE: DNA
<213> ORGANISM: Artificial Sequence
<220> FEATURE:
<223> OTHER INFORMATION: mouse primer_GAPDHr

<400> SEQUENCE: 18
cacggaaggc catgccagtg a                                           21

<210> SEQ ID NO 19
<211> LENGTH: 22
<212> TYPE: DNA
<213> ORGANISM: Artificial Sequence
<220> FEATURE:
<223> OTHER INFORMATION: mouse primer_OPNf

<400> SEQUENCE: 19
ctcgtgcagg aagaacagaa gc                                          22

<210> SEQ ID NO 20
<211> LENGTH: 23
<212> TYPE: DNA
<213> ORGANISM: Artificial Sequence
<220> FEATURE:
<223> OTHER INFORMATION: mouse primer_OPNr

<400> SEQUENCE: 20
gagtcaagtc agctggatga acc                                         23

<210> SEQ ID NO 21
<211> LENGTH: 22
<212> TYPE: DNA
<213> ORGANISM: Artificial Sequence
<220> FEATURE:
<223> OTHER INFORMATION: mouse primer_S100A8f

<400> SEQUENCE: 21
cccgtcttca agacatcgtt tg                                          22

<210> SEQ ID NO 22
<211> LENGTH: 22
<212> TYPE: DNA
<213> ORGANISM: Artificial Sequence
<220> FEATURE:
<223> OTHER INFORMATION: mouse primer_S100A8r

<400> SEQUENCE: 22
atatccaggg acccagccct ag                                          22

<210> SEQ ID NO 23
<211> LENGTH: 20
<212> TYPE: DNA
<213> ORGANISM: Artificial Sequence
<220> FEATURE:
<223> OTHER INFORMATION: mouse primer_Serpine2f

```
<400> SEQUENCE: 23
atgcctggga tgctggatgc                                                  20

<210> SEQ ID NO 24
<211> LENGTH: 20
<212> TYPE: DNA
<213> ORGANISM: Artificial Sequence
<220> FEATURE:
<223> OTHER INFORMATION: mouse primer_Serpiner

<400> SEQUENCE: 24
aacctctcct gccacactga                                                  20

<210> SEQ ID NO 25
<211> LENGTH: 20
<212> TYPE: DNA
<213> ORGANISM: Artificial Sequence
<220> FEATURE:
<223> OTHER INFORMATION: mouse primer_Tmsb4f

<400> SEQUENCE: 25
cagatcagac tctcctcgtt                                                  20

<210> SEQ ID NO 26
<211> LENGTH: 20
<212> TYPE: DNA
<213> ORGANISM: Artificial Sequence
<220> FEATURE:
<223> OTHER INFORMATION: mouse primer_Tmsb4r

<400> SEQUENCE: 26
tctctgctag ccagaccatc                                                  20

<210> SEQ ID NO 27
<211> LENGTH: 223
<212> TYPE: DNA
<213> ORGANISM: Artificial Sequence
<220> FEATURE:
<223> OTHER INFORMATION: mouse probe_BTNL2

<400> SEQUENCE: 27
atctgagcct ctcatcagaa ggaagtcgcc gcctgtggtt ttcgtcattc ttgttatttt      60
cctgattgct gctgtgtgtt tgttcattgg tccgccgcca ccgtttcacc ttgatcaggt     120
cgatagccat ggccagaggc agcaccacaa caggcagggt catccatagc aaagctatct     180
tggagtctga gagagggaaa cgggctgttt tctcctggcc cag                       223

<210> SEQ ID NO 28
<211> LENGTH: 344
<212> TYPE: DNA
<213> ORGANISM: Artificial Sequence
<220> FEATURE:
<223> OTHER INFORMATION: mouse probe_CysC

<400> SEQUENCE: 28
gcacccttct gcgagatgaa acactatagg gaaggagcac aagtaaggaa cagtctgcat      60
gatccttcta gactcagccc ttaggcattt ttgcagctga attttgtcag ggagtgtgtg     120
cctttccagg gcacgctgta gatctggaag gagcagagtg ccttcctcat cagatggggc     180
tggtcatgga aaggacagtc agtcaaattt gtctgggact tggtacatgt agttcggccc     240
atctccacat ccaaaaaata gttcactcca gccacgagct gcttacgagc tctcaccacc     300
tgtatggcgc ggctgtggta cgcatcgttg ctgcccttgt tgta                      344
```

<210> SEQ ID NO 29
<211> LENGTH: 452
<212> TYPE: DNA
<213> ORGANISM: Artificial Sequence
<220> FEATURE:
<223> OTHER INFORMATION: mouse probe_OPN

<400> SEQUENCE: 29

```
cagaagcttt tggttacaac ggtgtttgca tgaaacaaca gactaagcta agagcccaaa        60
atattacctc tctttctcta catacatata tccactgaac tgagaaatga gcagttagta       120
ttcctgctta accctcacta acactttttc ttgttttttac taaatgcaaa gtaaggaact       180 gtgttttgc ctcttcttta gttgacctca gaagatgaac tctctaattc atgagaaatt        240
cggaatttca gatacctatc atcttcctta ctcttagggt ctaggactag cttgtccttg       300
tggctgtgaa acttgtggct ctgatgttcc aggctggctt tggaacttgc ttgactatcg       360
atcacatccg actgatcggc actctcctgg ctctctttgg aatgctcaag tctgtgtgtt       420
tccagacttg gttcatccag ctgacttgac tc                                     452
```

<210> SEQ ID NO 30
<211> LENGTH: 347
<212> TYPE: DNA
<213> ORGANISM: Artificial Sequence
<220> FEATURE:
<223> OTHER INFORMATION: mouse probe_S100A8

<400> SEQUENCE: 30

```
atatccaggg acccagccct aggccagaag ctctgctact ccttgtggct gtctttgtga        60
gatgccacac ccacttttat caccatcgca aggaactcct cgaagttaat tgcattgtca       120
ctattgatgt ccaattctct gaacaagttt tcgatattta tattctgcac aaactgagga       180
cactcagtag tgaccatttt cttgaagtca ttccttgtaga gggcatggtg atttccttgt      240
atattggaat aattgtggta gacatcaatg aggttgctca aggccttctc cagttcagac       300
ggcattgtca cgaaagattt cctttcaaac gatgtcttga agacggg                     347
```

<210> SEQ ID NO 31
<211> LENGTH: 213
<212> TYPE: DNA
<213> ORGANISM: Artificial Sequence
<220> FEATURE:
<223> OTHER INFORMATION: mouse probe_Serpine2

<400> SEQUENCE: 31

```
aacctctcct gccacactga ttaatcctct cctggaaagt cacacatatc aacaggaatg        60
aaacaaagat gctgaacttg acagacagca aatactcgag agggttgtta acctagataa       120
ctgatcagta gtttaaagaa atcttctaga catcgtgaaa ccggcctgct catccttcac       180
tacagcatcc caggcatcca gcatcccagg cat                                    213
```

<210> SEQ ID NO 32
<211> LENGTH: 395
<212> TYPE: DNA
<213> ORGANISM: Artificial Sequence
<220> FEATURE:
<223> OTHER INFORMATION: mouse probe_Tmsb4

<400> SEQUENCE: 32

```
tctctgctag ccagaccatc agatgggtgg gagaggcagg ggaggccttc ctgctcagta        60
gttctgattc tttgatgtga aaggggcagc acagtcattt aaacttgatc caacctcttt       120
```

```
gcatcttaca aagttaaaca gctaaaagaa gtaaaataag aaggcaatgc tcgtggaatg      180
tacagtgcat attggcggcg ctcgcctcat tacgattcgc cagcttgctt ctcttgttca      240
attgtttctt ttgaaggcag aggattttc tcttgcgttt ctgttttctt caacttcgac       300
ttatcgaatt tctcgatctc agccatatcg ggtttgtcag acatggttgc tggaaggagc      360
cgagcgagct gcgcgaacga ggagagtctg atctg                                 395
```

<210> SEQ ID NO 33
<211> LENGTH: 22
<212> TYPE: DNA
<213> ORGANISM: Artificial Sequence
<220> FEATURE:
<223> OTHER INFORMATION: human primer_BTNL2f

<400> SEQUENCE: 33

```
gaggtgactg agatgcagat gg                                                22
```

<210> SEQ ID NO 34
<211> LENGTH: 20
<212> TYPE: DNA
<213> ORGANISM: Artificial Sequence
<220> FEATURE:
<223> OTHER INFORMATION: human primer_BTNL2r

<400> SEQUENCE: 34

```
ggagggctgg atgttgtgta                                                   20
```

<210> SEQ ID NO 35
<211> LENGTH: 20
<212> TYPE: DNA
<213> ORGANISM: Artificial Sequence
<220> FEATURE:
<223> OTHER INFORMATION: human primer_CysCf

<400> SEQUENCE: 35

```
ccagcaacga catgtaccac                                                   20
```

<210> SEQ ID NO 36
<211> LENGTH: 20
<212> TYPE: DNA
<213> ORGANISM: Artificial Sequence
<220> FEATURE:
<223> OTHER INFORMATION: human primer_CysCr

<400> SEQUENCE: 36

```
acaggtggat ttcgacaagg                                                   20
```

<210> SEQ ID NO 37
<211> LENGTH: 20
<212> TYPE: DNA
<213> ORGANISM: Artificial Sequence
<220> FEATURE:
<223> OTHER INFORMATION: human primer_OPNf

<400> SEQUENCE: 37

```
acagccagga ctccattgac                                                   20
```

<210> SEQ ID NO 38
<211> LENGTH: 20
<212> TYPE: DNA
<213> ORGANISM: Artificial Sequence
<220> FEATURE:
<223> OTHER INFORMATION: human primer_OPNr

<400> SEQUENCE: 38
acactatcac ctcggccatc        20

<210> SEQ ID NO 39
<211> LENGTH: 20
<212> TYPE: DNA
<213> ORGANISM: Artificial Sequence
<220> FEATURE:
<223> OTHER INFORMATION: human primer_S100A8f

<400> SEQUENCE: 39
atgccgtcta cagggatgac        20

<210> SEQ ID NO 40
<211> LENGTH: 20
<212> TYPE: DNA
<213> ORGANISM: Artificial Sequence
<220> FEATURE:
<223> OTHER INFORMATION: human primer_S100A8r

<400> SEQUENCE: 40
acgcccatct ttatcaccag        20

<210> SEQ ID NO 41
<211> LENGTH: 20
<212> TYPE: DNA
<213> ORGANISM: Artificial Sequence
<220> FEATURE:
<223> OTHER INFORMATION: human primer_Serpine2f

<400> SEQUENCE: 41
ctttgaggat ccagcctctg        20

<210> SEQ ID NO 42
<211> LENGTH: 20
<212> TYPE: DNA
<213> ORGANISM: Artificial Sequence
<220> FEATURE:
<223> OTHER INFORMATION: human primer_Serpine2r

<400> SEQUENCE: 42
tgcgtttctt tgtgttctcg        20

<210> SEQ ID NO 43
<211> LENGTH: 20
<212> TYPE: DNA
<213> ORGANISM: Artificial Sequence
<220> FEATURE:
<223> OTHER INFORMATION: human primer_Tmsb4f

<400> SEQUENCE: 43
attccacaag cattgccttc        20

<210> SEQ ID NO 44
<211> LENGTH: 20
<212> TYPE: DNA
<213> ORGANISM: Artificial Sequence
<220> FEATURE:
<223> OTHER INFORMATION: human primer_Tmsb4r

<400> SEQUENCE: 44
accccacttc ttccttcacc        20

<210> SEQ ID NO 45
<211> LENGTH: 108
<212> TYPE: DNA
<213> ORGANISM: Artificial Sequence

```
<220> FEATURE:
<223> OTHER INFORMATION: human probe_BTNL2

<400> SEQUENCE: 45
ggagggctgg atgttgtgta tcttcagtgc cacatttccc tttgcaatgc cattctctat    60
ccactctacc cagcctctgt actcctccat ctgcatctca gtcacctc                108

<210> SEQ ID NO 46
<211> LENGTH: 241
<212> TYPE: DNA
<213> ORGANISM: Artificial Sequence
<220> FEATURE:
<223> OTHER INFORMATION: human probe_CysC

<400> SEQUENCE: 46
acaggtggat ttcgacaagg tcattgtgcc ctgccaaggc acagcgtaga tctggaaaga    60
gcagaatgct ttccttttca gatgtggctg gtcatggaag gggcagttgt ccaagttggg   120
ctgggtcttg gtacacgtgg ttcggcccag ctccacgtcc aagaagtagt tcaccccagc   180
tacgatctgc ttgcgggcgc gcaccacctg cagcgcgcgg ctgtggtaca tgtcgttgct   240
g                                                                  241

<210> SEQ ID NO 47
<211> LENGTH: 197
<212> TYPE: DNA
<213> ORGANISM: Artificial Sequence
<220> FEATURE:
<223> OTHER INFORMATION: human probe_OPN

<400> SEQUENCE: 47
cacactatca cctcggccat catatgtgtc tactgtgggg acaactggag tgaaaacttc    60
ggttgctggc aggtccgtgg gaaaatcagt gaccagttca tcagattcat cagaatggtg   120
agactcatca gactggtgag aatcatcagt gtcatctaca tcatcagagt cgttcgagtc   180
aatggagtcc tggctgt                                                 197

<210> SEQ ID NO 48
<211> LENGTH: 161
<212> TYPE: DNA
<213> ORGANISM: Artificial Sequence
<220> FEATURE:
<223> OTHER INFORMATION: human probe_S100A8

<400> SEQUENCE: 48
cacgcccatc tttatcacca gaatgaggaa ctcctggaag ttaactgcac catcagtgtt    60
gatatccaac tctttgaacc agacgtctgc acccttttc ctgatatact gaggacactc    120
ggtctctagc aatttcttca ggtcatccct gtagacggca t                      161

<210> SEQ ID NO 49
<211> LENGTH: 202
<212> TYPE: DNA
<213> ORGANISM: Artificial Sequence
<220> FEATURE:
<223> OTHER INFORMATION: human probe_Serpine2

<400> SEQUENCE: 49
tgccacgaaa gtgcgtttct ttgtgttctc gggttggaac cgtgatttcc acagacccctt   60 gaaatacact gcgttgacga ggaccagtct ggtgagcaca ccatcaataa gatctgggga   120
cagcagattg tcaatcatat ccctggtttc attttaacc catgcattga tggaatcaca   180
ggcagaggct ggatcctcaa ag                                           202
```

```
<210> SEQ ID NO 50
<211> LENGTH: 213
<212> TYPE: DNA
<213> ORGANISM: Artificial Sequence
<220> FEATURE:
<223> OTHER INFORMATION: human probe_Tmsb4

<400> SEQUENCE: 50 cacccactt   cttccttcac   caacatgcaa   gttctttcct   tccctgccag   ccagatagat        60
agacagatgg  gaaaggcagg   cgcggccttc   gttgtcagta   gttctttgat   gtgaaagggg       120
cagcacagtc  atttaaactt   gatccaacct   ctttgcatct   tacaaagtta   aacagctaaa       180
agaagtaaaa  taagaaggca   atgcttgtgg   aat                                        213
```

SERPINE2 AS A BIOMARKER FOR IGA NEPHROPATHY

FIELD OF THE INVENTION

The preset invention relates to biomarkers for IgA nephropathy and applications thereof.

BACKGROUND OF THE INVENTION

IgA nephropathy is the most frequent type of glomerular disorders worldwide, up to 60% of the patients eventually progressing to either end-stage renal disease or chronic renal failure after 20 years of follow-up. Although the pathogenesis of IgA nephropathy is still largely unknown, an initial response of intrinsic glomerular cells to IgA immune complexes, including abnormal glycosylated IgA1 as "neoantigen", plays a primary role, whereby triggering release of cytokines and growth factors in the glomerulus affected. To date, a renal biopsy is required for diagnosis and prognosis of IgA nephropathy, but many patients might be reluctant to accept the invasive procedure, which might cause not diagnosed or delayed diagnosed until the clinical features are outward or a disease progression has already developed. Unfortunately, renal biopsy also entails risk for serious bleeding complications, which is a major negative impact on the diagnosis and prognosis for patients with the glomerular disorder.

There is still a need for additional biomarkers useful for diagnosis and prognosis of IgA nephropathy, especially in a non-invasive way.

BRIEF SUMMARY OF THE INVENTION

In one aspect, the present invention provides a method for diagnosing IgA nephropathy in a subject, comprising analyzing a test sample obtained from the subject for the expression level of one or more genes selected from the group consisting of thymosin β4 (Tmsb4), serine or cysteine proteinase inhibitor clade E member 2 (Serpine2), secreted phosphoprotein 1 (OPN), butyrophilin-like-2 (BTNL2), S100 calcium binding protein A8 (S100A8), Cystatin C (CysC), and any combination thereof, wherein the expression level of the one or more genes in the test sample that is increased relative to the expression level of the one or more genes in a normal sample indicates that the subject is afflicted with IgA nephropathy.

In another aspect, the present invention provides a method for determining a prognosis in a patient afflicted with IgA nephropathy, comprising analyzing a test sample obtained from the subject for the expression level of one or more genes selected from the group consisting of Tmsb4, Serpine2, OPN, BTNL2, S100A8, CysC, and any combination thereof, wherein the expression level of the one or more genes in the test sample that is increased relative to the expression level of the one or more genes in a normal sample is indicative of an unfavorable prognosis.

The various embodiments of the present invention are described in details below. Other characteristics of the present invention will be clearly presented by the following detailed descriptions and drawings about the various embodiments and claims.

It is believed that a person of ordinary knowledge in the art where the present invention belongs can utilize the present invention to its broadest scope based on the descriptions herein with no need of further illustration. Therefore, the following descriptions should be understood as of demonstrative purpose instead of limitative in any way to the scope of the present invention.

BRIEF DESCRIPTION OF THE SEVERAL VIEWS OF THE DRAWINGS

For the purpose of illustrating the invention, there are shown in the drawings embodiments which are presently preferred. It should be understood, however, that the invention is not limited to the preferred embodiments shown.

In the drawings.

***p<0.005 represent statistical significance compared to the normal control (day 0). The symbol "#" means data not detectable.

Figure 6:
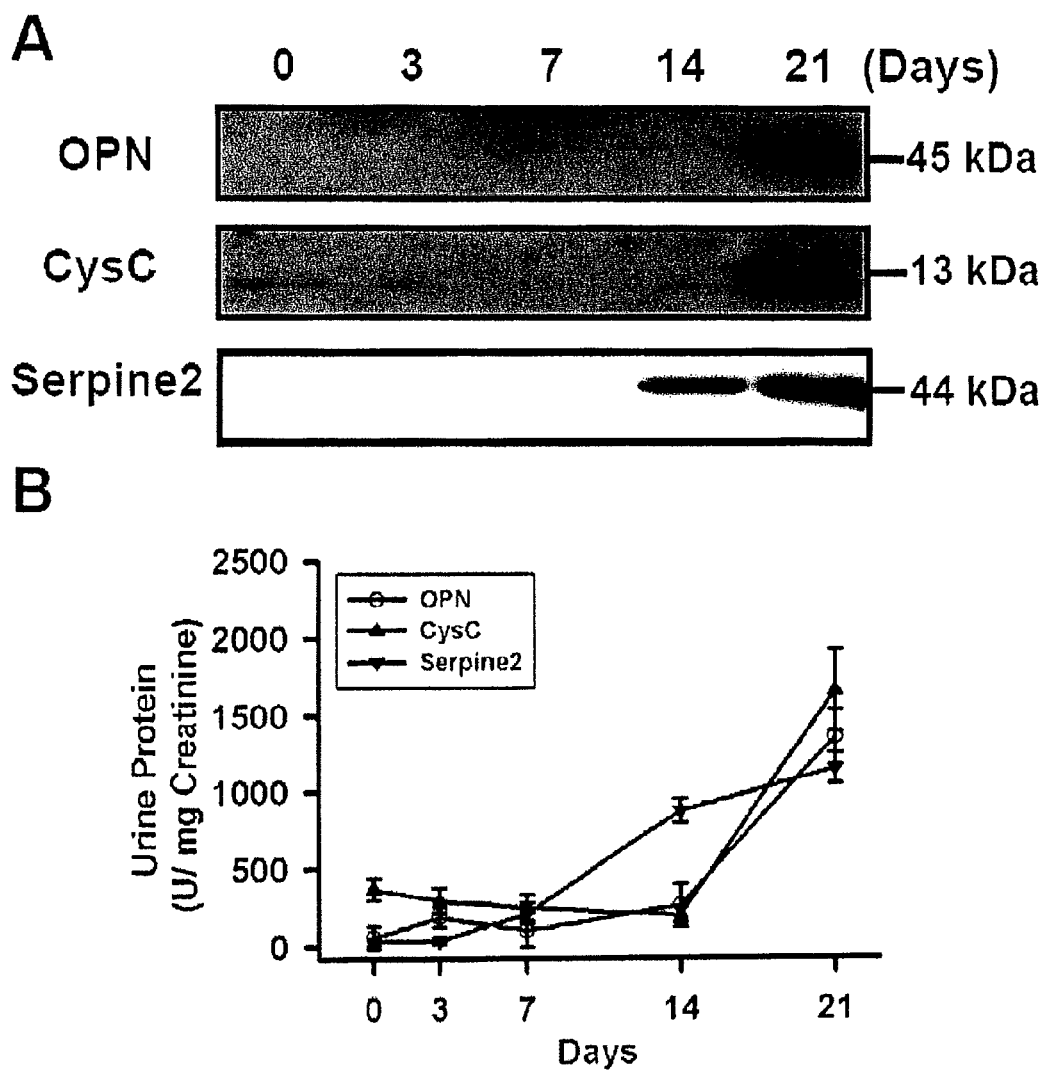

FIG. 6 shows the detection of urine levels of OPN, CysC and Serpine2 of the Prg-IgAN model in a time-course manner. (A) is the representative Western blots of the urine samples, probed with antibodies against OPN, CysC and Serpine2, respectively. Molecular weight markers are shown on the right. (B) is the quantitative analysis as represented by the ratio of the density to urinary creatinine. Each point represents the mean±SE (day 0).

Figure 7:
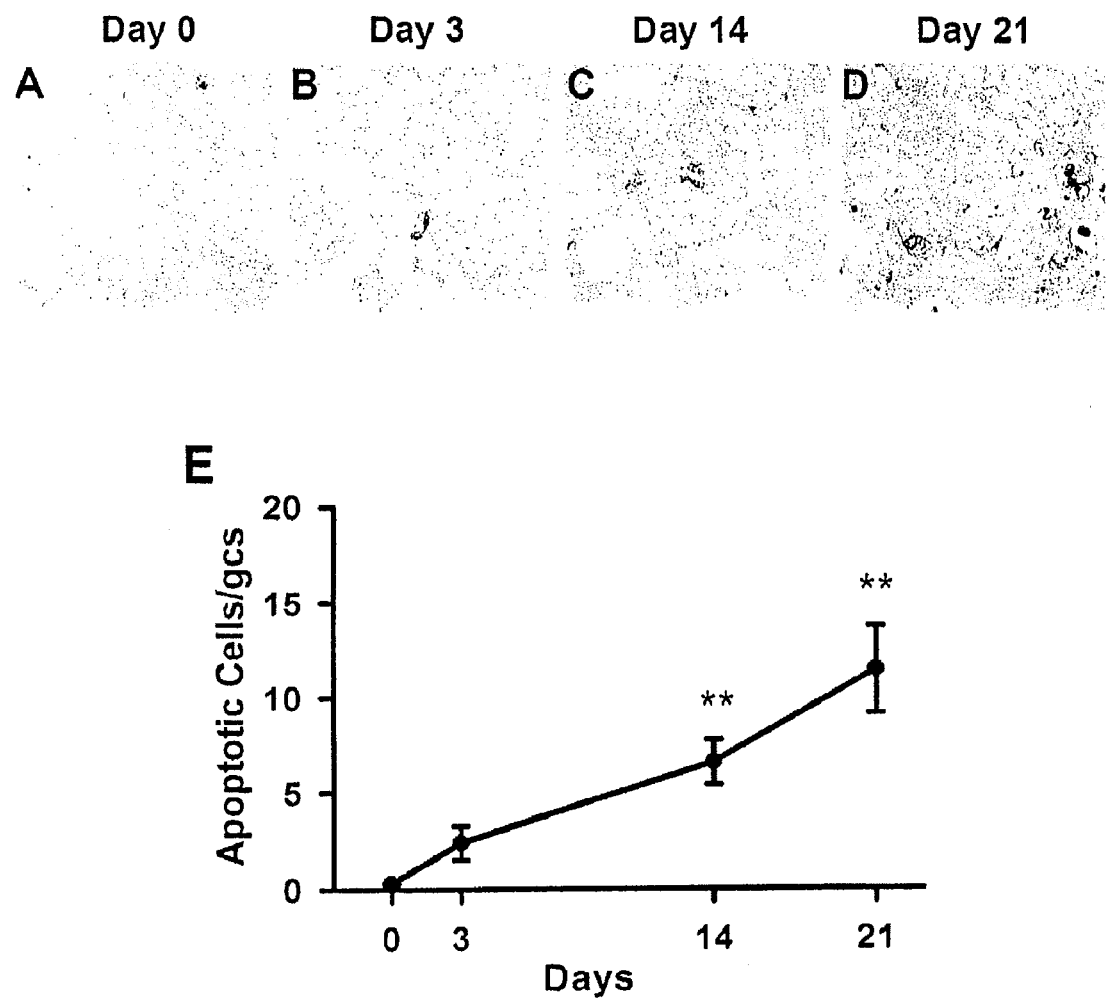

FIG. 7 shows the renal terminal deoxynucleotidyl transferase dUTP nick end labeling (TUNEL) analysis of the Prg-IgAN model in a time-course manner. (A) to (D) represent the kidney tissues on day 0, 3, 14, or 21 showing cell apoptosis. Original magnification is ×400 each. (E) represents the scoring of the apoptotic cells. **p<0.01 represents statistical significance compared to the normal control (day 0).

Figure 8:
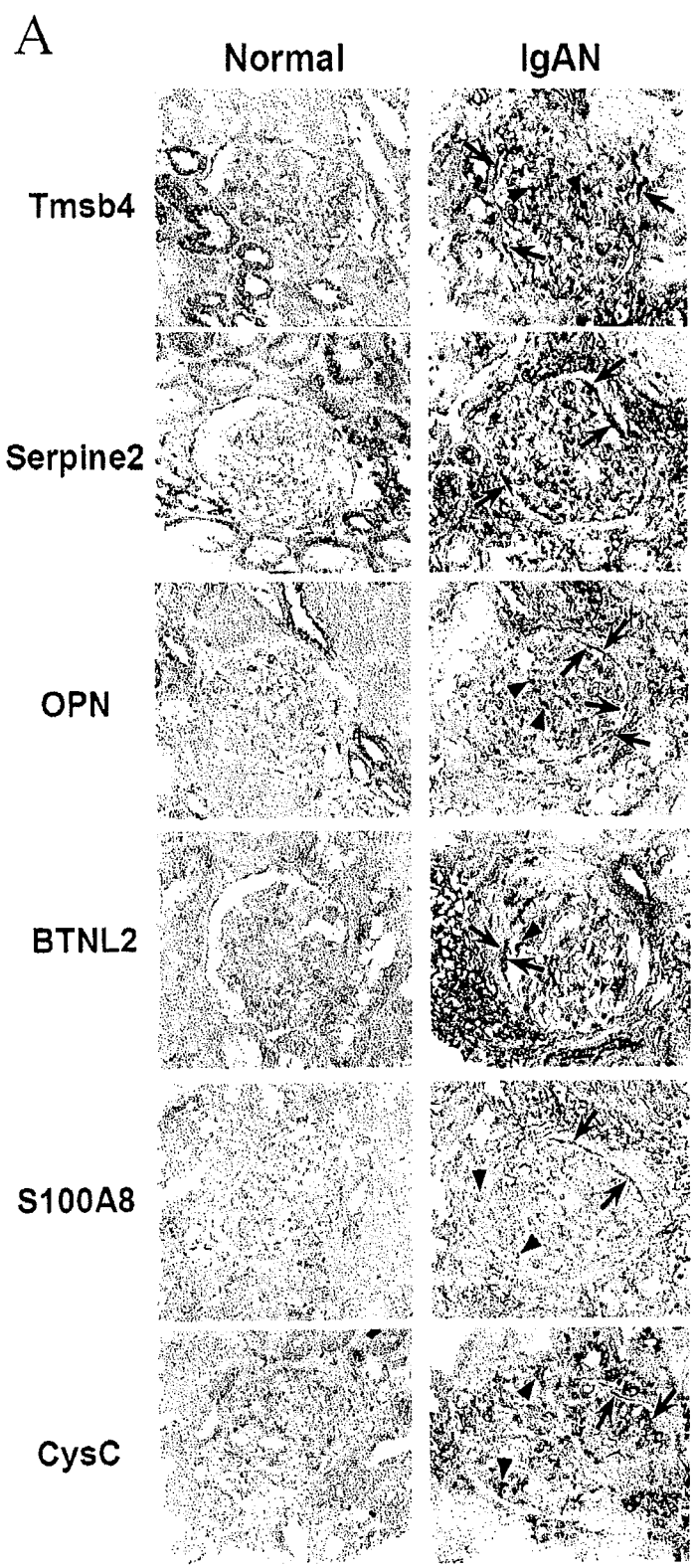
Figure 8:
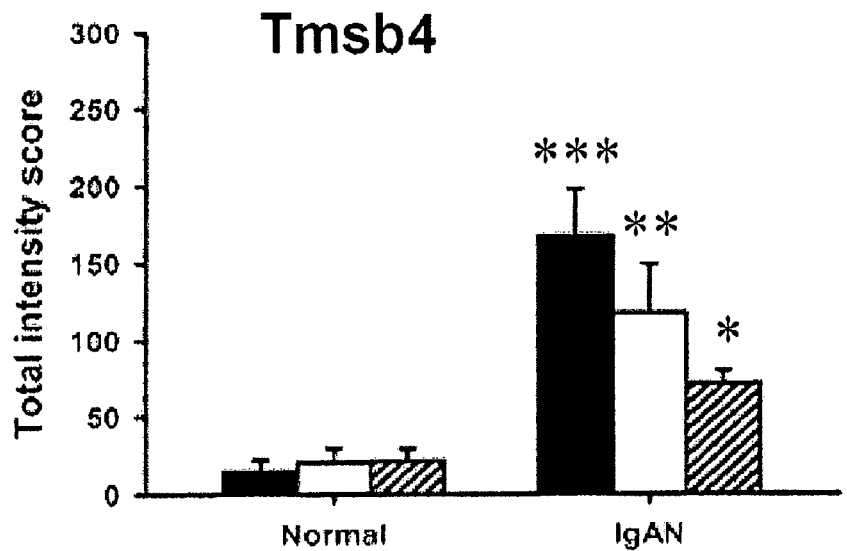
Figure 8:
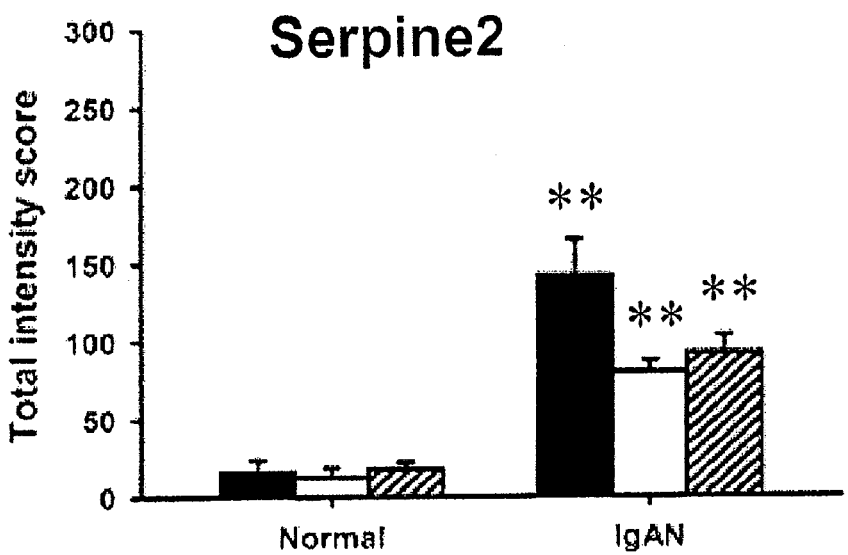
Figure 8:
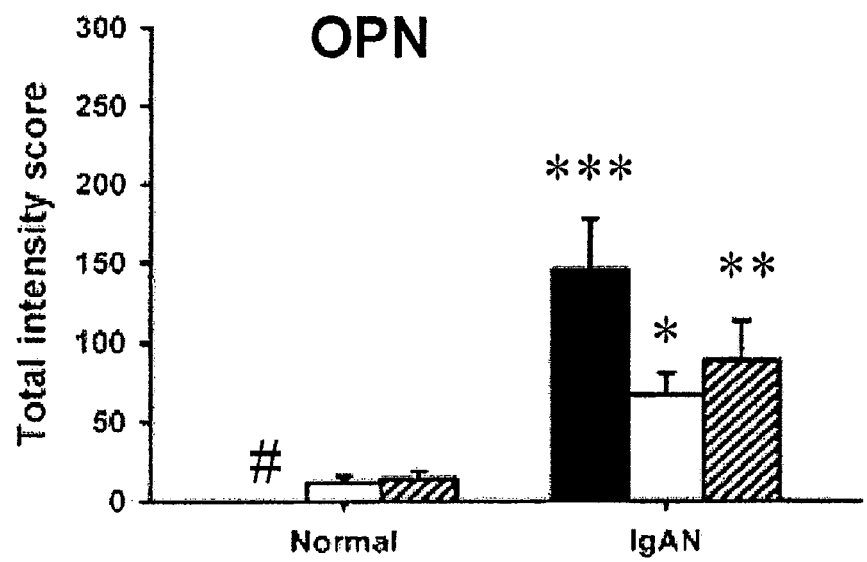
Figure 8:
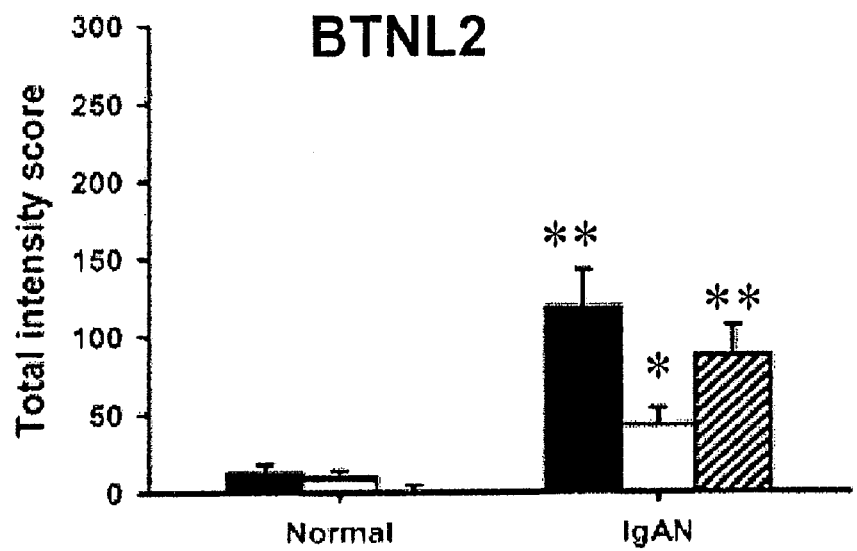
Figure 8:
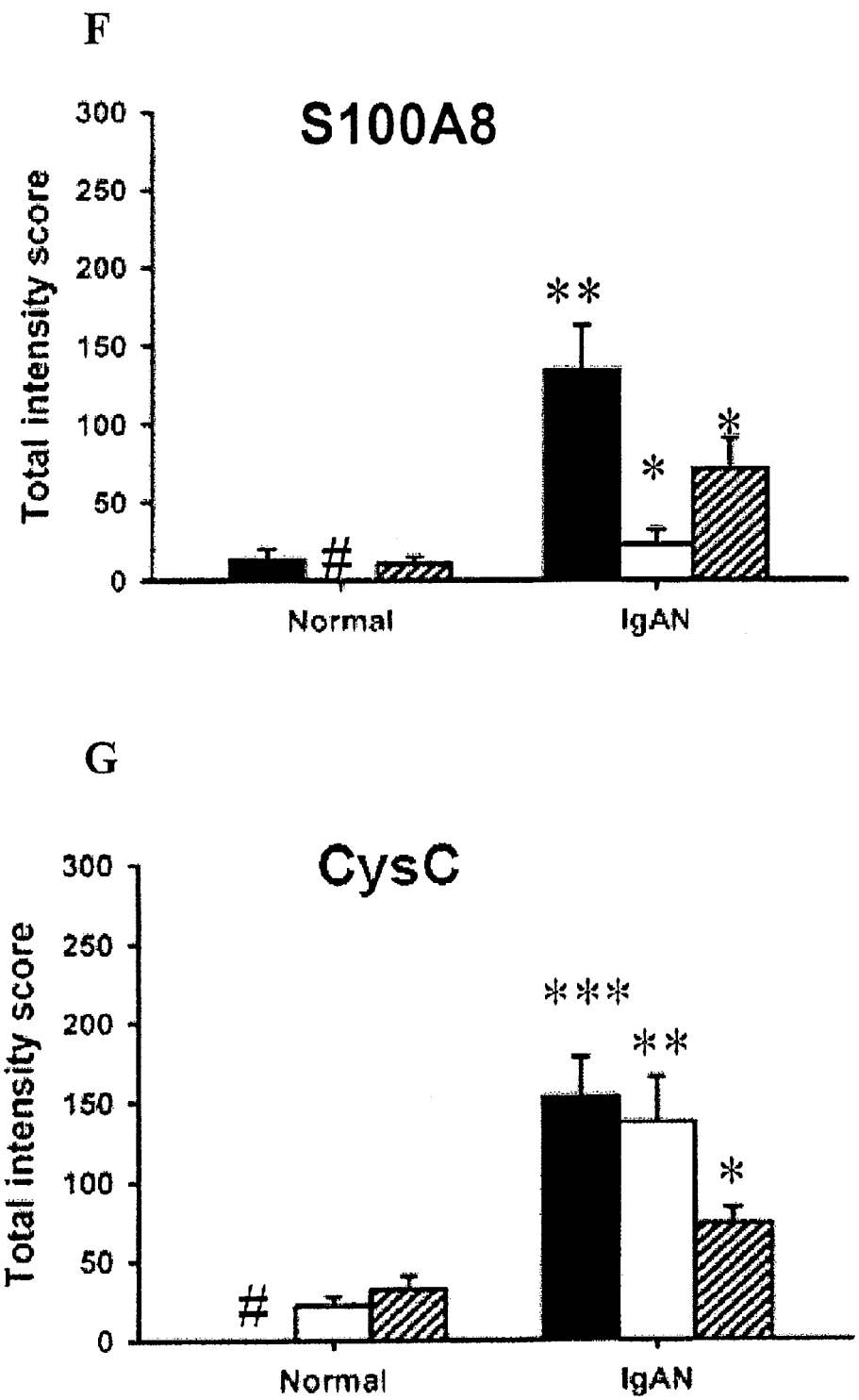

FIG. 8 shows the renal ISH results for the IgAN patients with unfavorable prognosis factors (UPF). (A) represents the results for Tmsb4, Serpine2, OPN, BTNL2, S100A8, and CysC. Arrows indicate parietal epithelial cells, and arrowheads indicate podocytes. Original magnification is ×400 each. (B) to (G) represent the semi-quantitative analysis of cellular mRNA expression. The scoring was performed for the three major components: parietal epithelial cells (solid bars), podocytes (open bars) and mesangial cells (hatched bars). Each bar represents the mean±SE. *p<0.05, p<0.01 and p<0.005 represent statistical significance compared to normal control. The symbol "#" means data not detectable.

Figure 9:
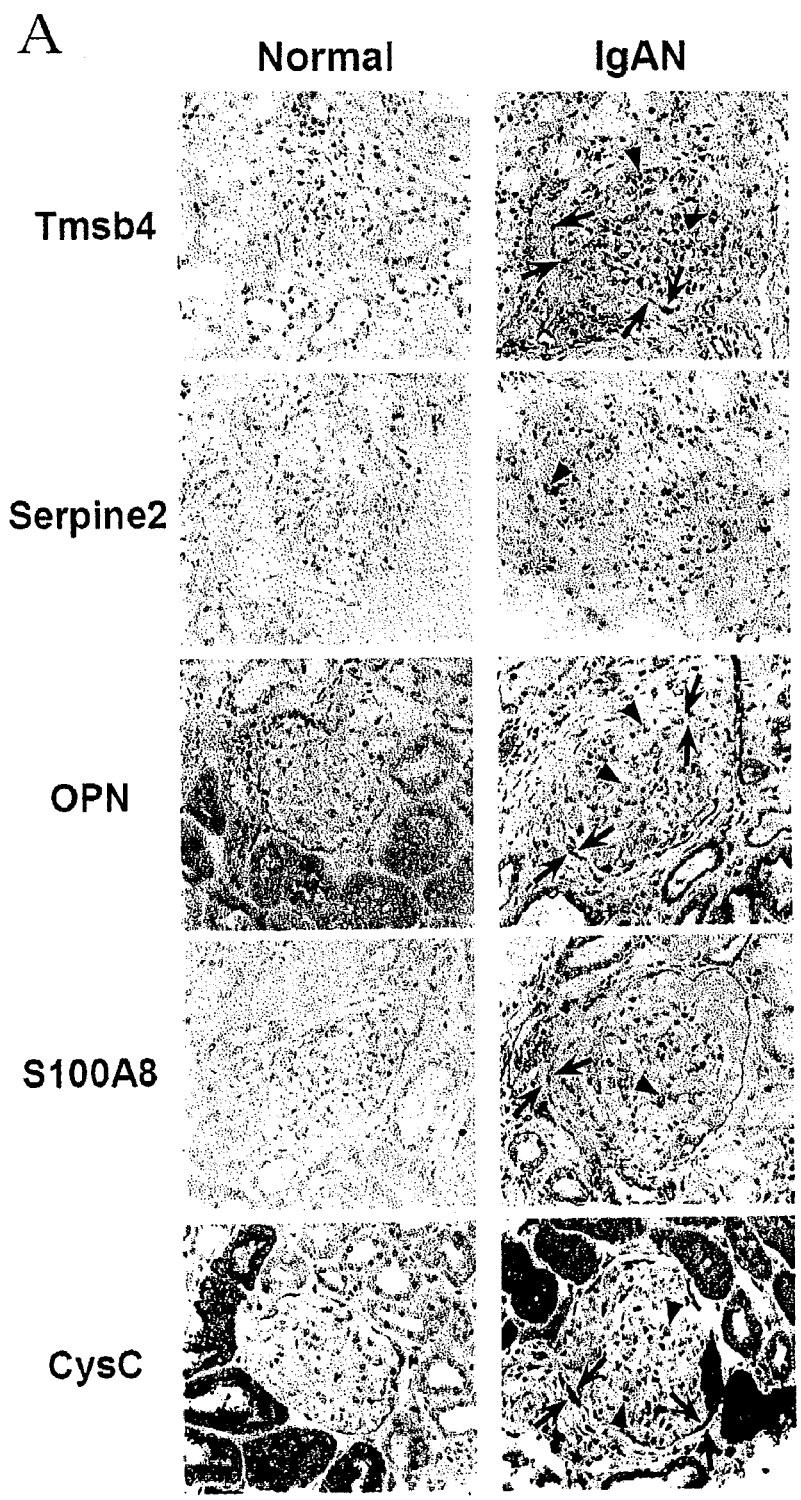
Figure 9:
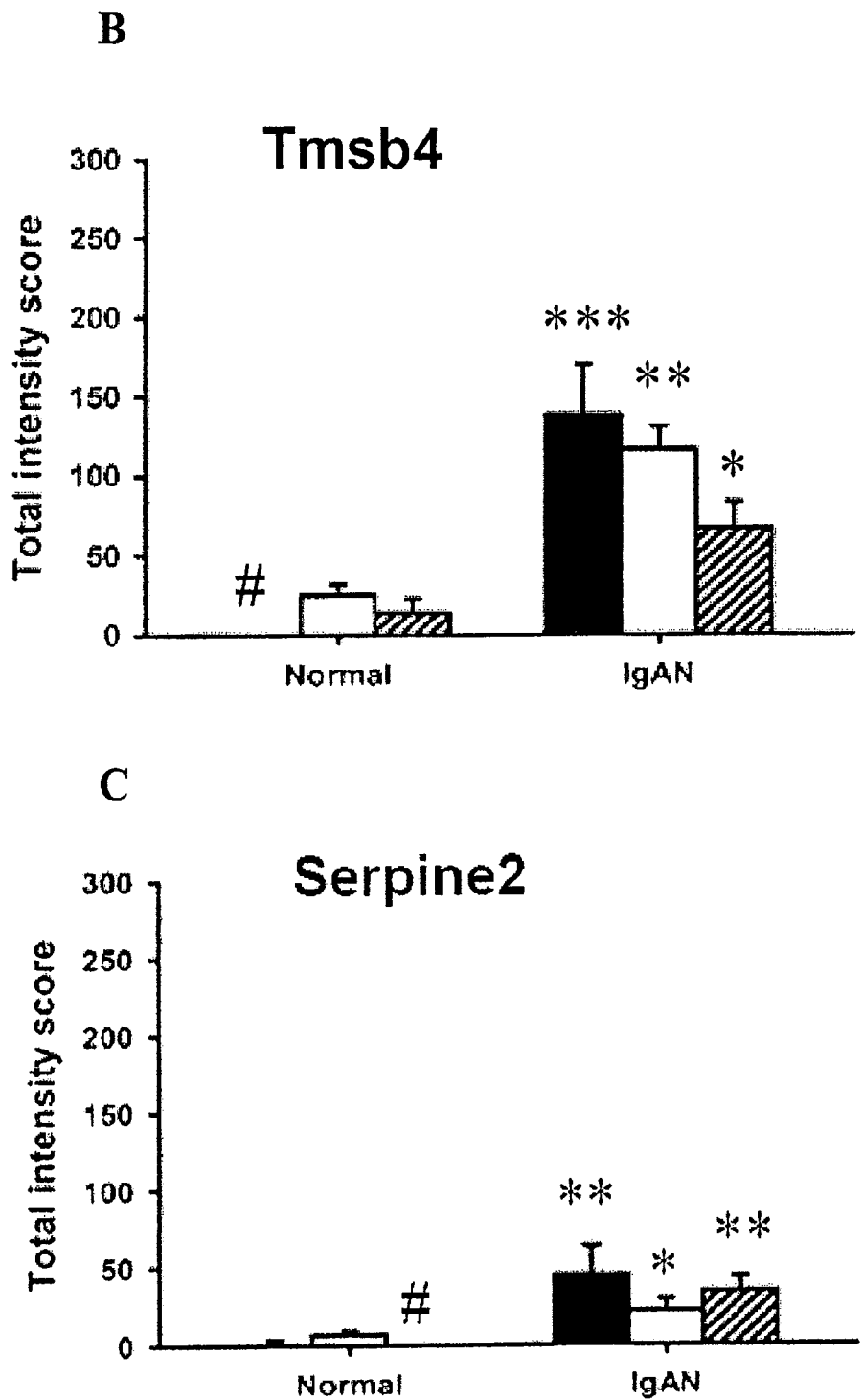
Figure 9:
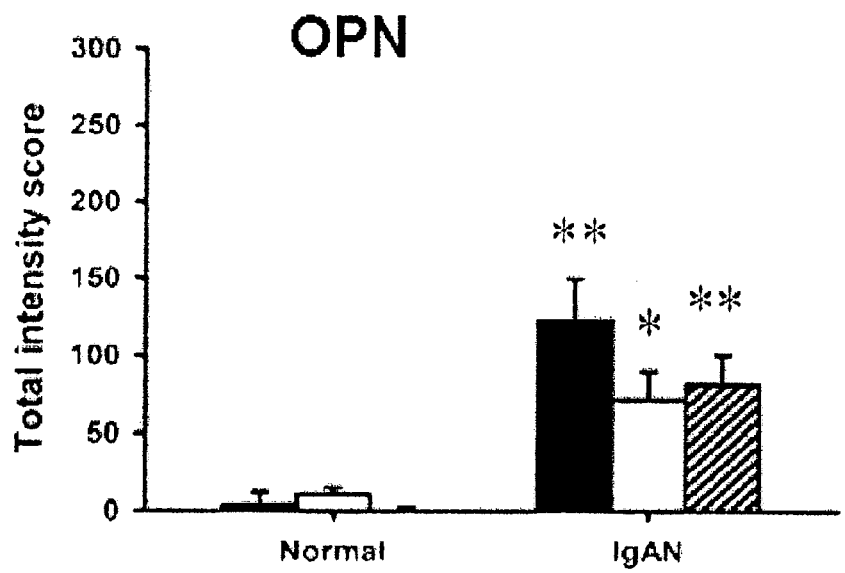
Figure 9:
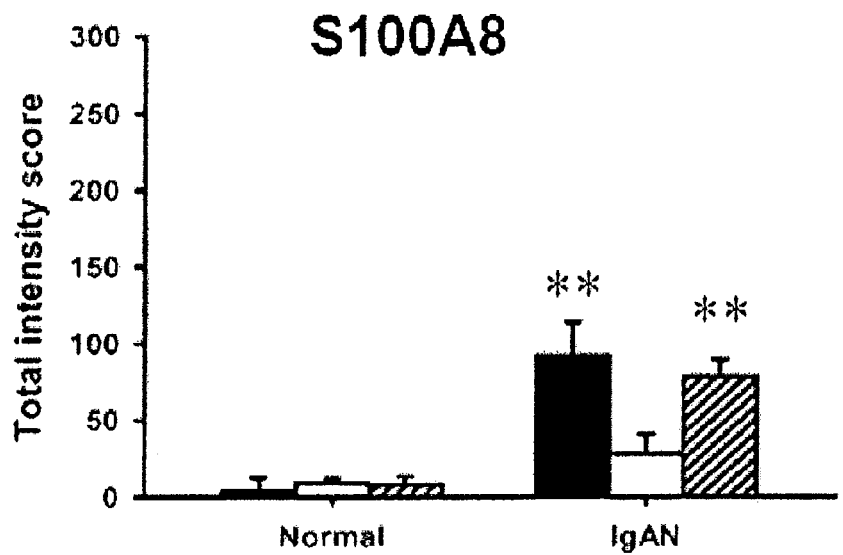
Figure 9:
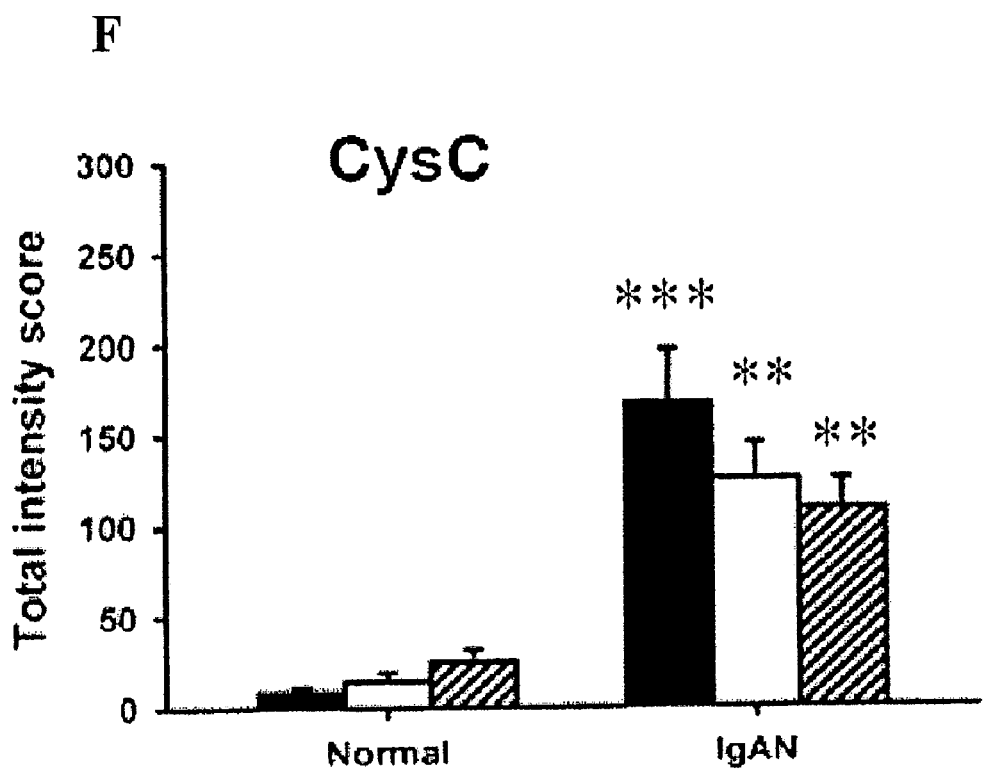

FIG. 9 shows the renal IHC results for IgAN patients with UPF. (A) represents the results for Tmsb4, Serpine2, OPN, BTNL2, S100A8, and CysC. Arrows indicate parietal epithelial cells, and arrowheads indicate podocytes. Original magnification is ×400 each. (B) to (F) represent the semi-quantitative analysis of cellular protein expression. The scoring was performed for the three major components: parietal epithelial cells (solid bars), podocytes (open bars) and mesangial cells (hatched bars). Each bar represents the mean±SE. *p<0.05, p<0.01, and p<0.005 represent statistical significance compared to normal control. The symbol "#" means data not detectable.

Figure 10:
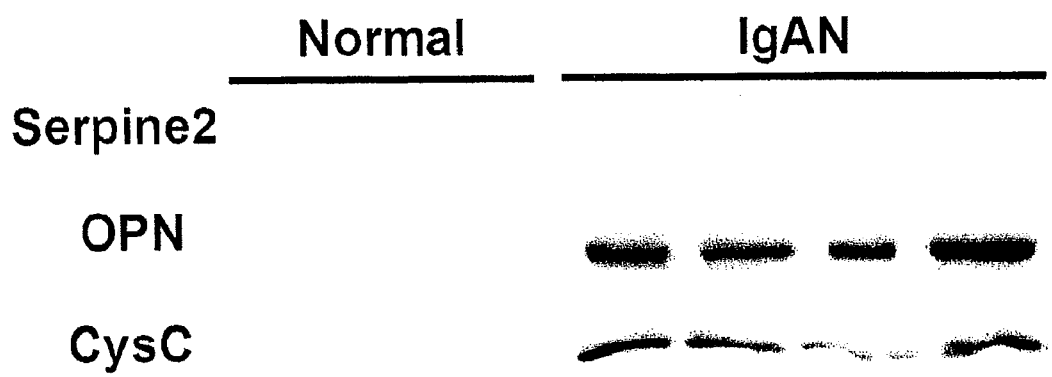
Figure 10:
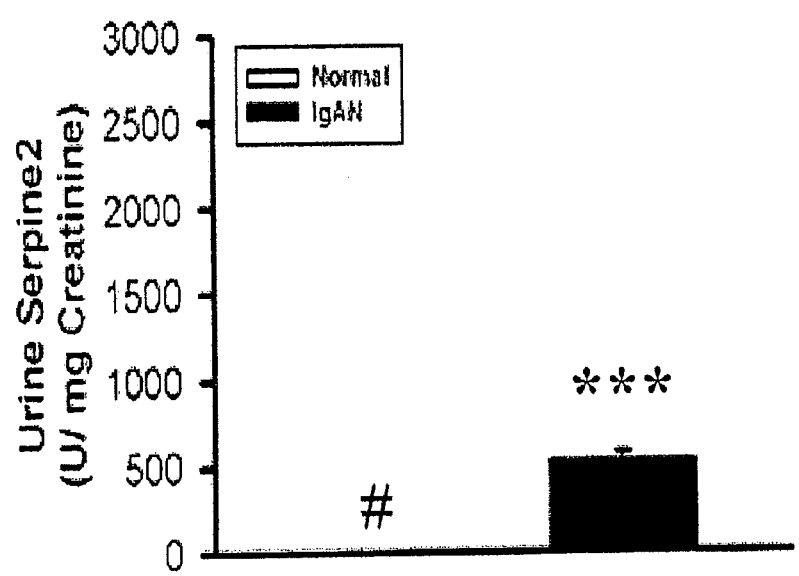
Figure 10:
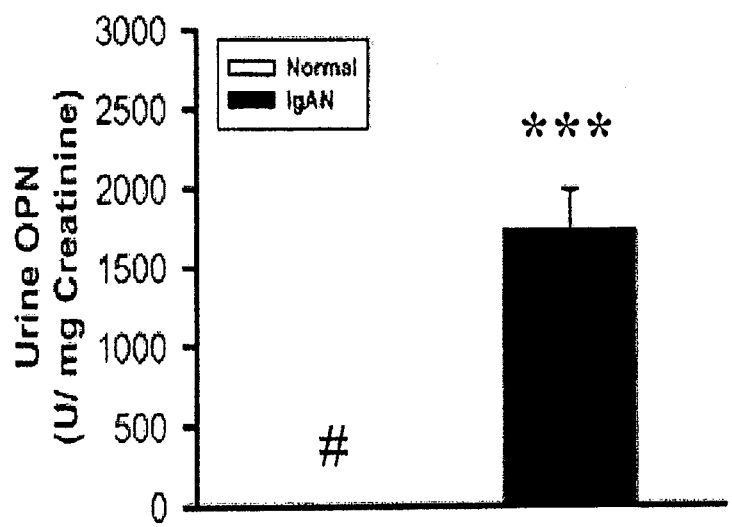
Figure 10:
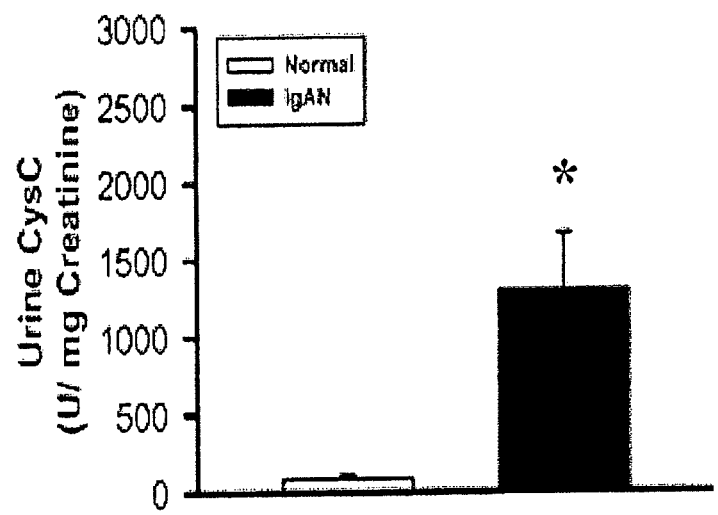
Figure 10:
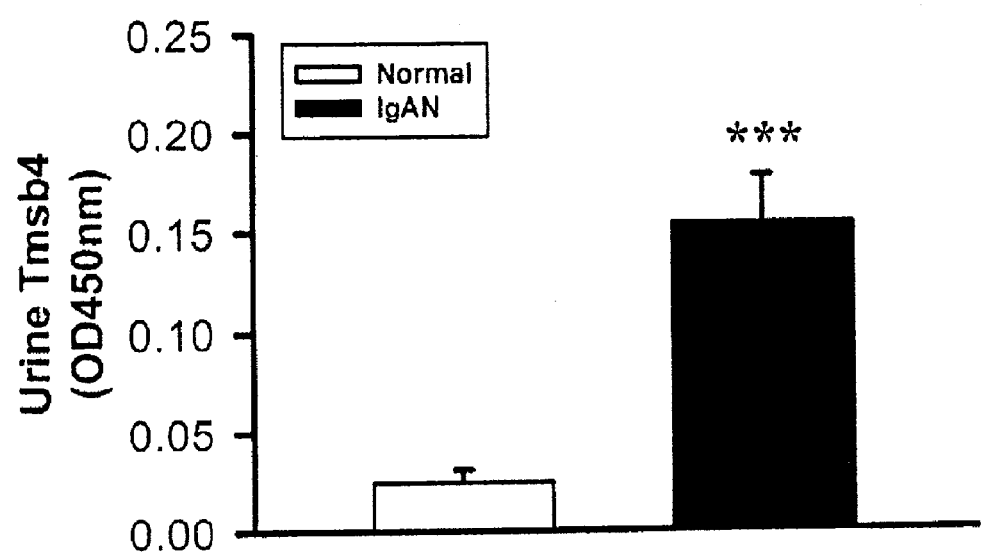

FIG. 10 shows the detection of urine levels of Serpine2, OPN, CysC, and Tmsb4 for samples from normal subjects and IgAN patients with UPF. (A) indicates representative Western blots of the urine samples, probed with antibodies against OPN, CysC and Serpine2, respectively; (B), (C) and (D) indicate quantitative analysis for Serpine2, OPN and CysC, respectively, shown as the ratio of the density to urinary Cr; and (E) shows the ELISA results for Tmsb4. *p<0.05 and ***p<0.005 represent statistical significance compared to normal control. The symbol "#" means data not detectable.

DETAILED DESCRIPTION OF THE INVENTION

Unless defined otherwise, all technical and scientific terms used herein have the same meaning as commonly understood by a person skilled in the art to which this invention belongs. All publications mentioned herein are incorporated herein by reference to disclose and describe the methods and/or materials in connection with which the publications are cited.

As used herein, the singular forms "a", "an", and "the" include plural referents unless the context clearly dictates otherwise. Thus, for example, reference to reference to "a sample" includes a plurality of such samples and equivalents thereof known to those skilled in the art.

Definition

The terms "nucleic acid fragment," "nucleic acid" and "polynucleotide," used interchangeably herein, refer to a polymer composed of nucleotide units, including naturally occurring nucleic acids, such as deoxyribonucleic acid ("DNA") and ribonucleic acid ("RNA") as well as nucleic acid analogs including those which have non-naturally occurring nucleotides. Thus, these terms include, but are not limited to, single-, double-, or multi-stranded DNA or RNA, genomic DNA, cDNA, mRNA, DNA-RNA hybrids, or a polymer comprising purine and pyrimidine bases or other natural, chemically or biochemically modified, non-natural, or derivatized nucleotide bases. It will be understood that when a nucleic acid fragment is represented by a DNA sequence (i.e., A, T, G, C), this also includes an RNA sequence (i.e., A, U, G, C) in which "U" replaces "T."

The term "primer" as used herein refers to a specific oligonucleotide sequence which is complementary to a target nucleotide sequence and used to hybridize to the target nucleotide sequence. A primer serves as an initiation point for nucleotide polymerization catalyzed by either DNA polymerase, RNA polymerase or reverse transcriptase. For example, primers for Tmsb4, Serpine2, OPN, BTNL2, S100A8, and CysC, as used herein, respectively, are those which are capable to hybridize to the nucleotide sequence of the individual target genes to initiate nucleotide polymerization and produce the nucleotide products as expected based on the design of the sequences of the primers.

The term "probe" as used herein refers to a defined nucleic acid segment (or nucleotide analog segment, e.g., polynucleotide as defined herein) which can be used to identify a specific polynucleotide sequence present in samples during hybridization, said nucleic acid segment comprising a nucleotide sequence complementary of the specific polynucleotide sequence to be identified. Typically, a probe can produce a detectable signal since it is labeled in some way, for example, by incorporation of a reporter molecule such as a fluorophore or radionuclide. For example, probes for Tmsb4, Serpine2, OPN, BTNL2, S100A8, and CysC, as used herein, respectively, are those which are capable to specifically hybridize to the corresponding nucleotide sequence of the individual target genes and produce detectable signals caused by such hybridization.

The term "hybridization" as used herein shall include any process by which a strand of nucleic acid joins with a complementary strand through base pairing. Relevant technologies are well known in the art and described in, for example, Sambrook et al., Molecular Cloning: A Laboratory Manual, $2^{nd}$ ed., Cold Spring Harbor Laboratory Press (1989), and Frederick M. A. et al., Current Protocols in Molecular Biology, John Wiley & Sons, Inc. (2001). Typically, stringent conditions are selected to be about 5 to 30° C. lower than the thermal melting point $(T_m)$ for the specified sequence at a defined ionic strength and pH. More typically, stringent conditions are selected to be about 5 to 15° C. lower than the $T_m$ for the specified sequence at a defined ionic strength and pH. For example, stringent hybridization conditions will be those in which the salt concentration is less than about 1.0 M sodium (or other salts) ion, typically about 0.01 to about 1 M sodium ion concentration at about pH 7.0 to about pH 8.3 and the temperature is at least about 25° C. for short probes (e.g., 10 to 50 nucleotides) and at least about 55° C. for long probes (e.g., greater than 50 nucleotides). An exemplary non-stringent or low stringency condition for a long probe (e.g., greater than 50 nucleotides) would comprise a buffer of 20 mM Tris, pH 8.5, 50 mM KCl, and 2 mM $MgCl_2$, and a reaction temperature of 25° C.

The term "encode" as used herein refers to the inherent property of specific sequences of nucleotides in a polynucleotide (e.g., a gene, a cDNA, or an mRNA) to serve as templates for synthesis of a gene product having either a defined sequence of nucleotides (i.e., rRNA, tRNA and mRNA) or a defined sequence of amino acids and the biological properties resulting therefrom.

The term "expression" as used herein refers to the realization of genetic information encoded in a gene to produce a gene product such as an unspliced RNA, an mRNA, a splice variant mRNA, a polypeptide or protein, a post-translationally modified polypeptide, a splice variant polypeptide and so on.

The term "expression level" refers to the amount of a gene product expressed by a particular gene in cells which can be determined by any suitable method known in the art.

The terms "polypeptide" and "protein," used interchangeably herein, refer to a polymeric form of amino acids of any length, which can include coded and non-coded amino acids, chemically or biochemically modified or derivatized amino acids, and polypeptides having modified peptide backbones.

The term "antibody" means an immunoglobulin protein which is capable of binding an antigen. Antibody as used herein is meant to include the entire antibody as well as any antibody fragments (e.g., F(ab').sub.2, Fab', Fab, Fv) capable of binding the epitope, antigen, or antigenic fragment of interest. Antibodies of the invention are immunoreactive or immunospecific for and therefore specifically and selectively bind to a protein of interest, e.g., Tmsb4, Serpine2, OPN, BTNL2, S100A8, and CysC of humans. Antibodies for the proteins of interest are preferably immunospecific, i.e., not substantially cross-reactive with related materials, although they may recognize their homologs across species. The term "antibody" encompasses all types of antibodies (e.g., monoclonal and polyclonal).

The terms "subject," "individual" and "patient," used interchangeably herein and refer to any mammalian subject for whom diagnosis, prognosis, treatment, or therapy is desired, particularly humans. Other subjects may include cattle, dogs, cats, guinea pigs, rabbits, rats, mice, horses, and so on.

"Diagnosis" as used herein generally includes determination as to whether a subject is likely affected by a given disease, disorder or dysfunction. The skilled artisan often makes a diagnosis on the basis of one or more diagnostic indicators, i.e., a marker, the presence, absence, or amount of which is indicative of the presence or absence of the disease, disorder or dysfunction.

"Prognosis" as used herein generally refers to a prediction of the probable course and outcome of a clinical condition or disease. A prognosis of a patient is usually made by evaluating factors or symptoms of a disease that are indicative of a favorable or unfavorable course or outcome of the disease. It is understood that the term "prognosis" does not necessarily refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition. Prognosis can be expressed in various ways; for example prognosis can be expressed as a percent chance that a patient will progress to end-stage renal disease or chronic renal failure after one year, five years, ten years or the like.

The terms "favorable prognosis" and "positive prognosis," or "unfavorable prognosis" and "negative prognosis" as used herein are relative terms for the prediction of the probable course and/or likely outcome of a condition or a disease. In general, a favorable or positive prognosis predicts a better outcome for a condition than an unfavorable or negative prognosis. Typical examples of a favorable or positive prognosis includes a better than average cure rate and a lower propensity for progression into end-stage renal disease or chronic renal failure. On the other hand, typical examples of an unfavorable or negative prognosis includes a worse than average cure rate, a higher propensity for progression into end-stage renal disease or chronic renal failure, and the like. For example, if a prognosis is that a patient has a 50% probability of progressing into end-stage renal disease or chronic renal failure within one year, while the average patient with the same disease has only a 25% probability of such progression, then that patient exhibits a negative prognosis.

Methods of the Invention

The present invention features novel biomarkers for IgA nephropathy, identified by a glomerulus-based approach, including thymosin β4 (Tmsb4), serine or cysteine proteinase inhibitor clade E member 2 (Serpine2), secreted phosphoprotein 1 (OPN), butyrophilin-like-2 (BTNL2), S100 calcium binding protein A8 (S100A8) and Cystatin C (CysC). According to the invention, these biomarkers are highly associated with the unfavorable progression of IgA nephropathy and therefore are useful for diagnosing and predicting unfavorable progression of the glomerular disease. In addition, since the biomarkers of the invention are identified by a glomerulus-based approach as described below, it is believed that they are more reliable for diagnosis and prognosis of IgA nephropathy than renal histopathology-based prediction as currently used in the art.

Accordingly, in one aspect, the present invention provides a method for diagnosing or, determining the risk of having, IgA nephropathy in a subject, comprising analyzing a test sample obtained from the subject for the expression level of one or more genes selected from the group consisting of Tmsb4, Serpine2, OPN, BTNL2, S100A8, CysC, and any combination thereof, wherein the expression level of the one or more genes in the test sample that is increased relative to the expression level of the one or more genes in a normal sample indicates that the subject is afflicted with or, at risk of having, IgA nephropathy.

In another aspect, the present invention provides a method for determining a prognosis in a patient afflicted with IgA nephropathy, comprising analyzing a test sample obtained from the subject for the expression level of one or more genes selected from the group consisting of Tmsb4, Serpine2, OPN, BTNL2, S100A8, CysC, and any combination thereof, wherein the expression level of the one or more genes in the test sample that is increased relative to the expression level of the one or more genes in a normal sample is indicative of an unfavorable prognosis.

As used herein, IgA nephropathy refers to a kidney disease characterized by IgA1 deposits within the kidney. The most common histopathologic alteration associated with IgAN is focal or diffuse expansion of mesangial regions with proliferative cells and extracellular matrix. In addition, a wide variety of lesions identified by light microscopy may be seen in patients with more severe lesions, including diffuse endocapillary proliferation, segmental sclerosis, segmental necrosis, and cellular crescent formation. Different prognosis is found in patients with IgA nephropathy. Several factors have been confirmed to highly correlated with an unfavorable prognosis of IgA nephropathy including hematuria, proteinuria, moderate hypercellularity, glomerulosclerosis, tubulointerstitial inflammation, and a diffuse glomerular co-deposition of IgG and/or IgM as well as complement components 3 (C3).

Tmsb4 is a member of the thymosin family and one of the main actin sequestering proteins, which is known to involve in several biological functions such as inducing angiogenesis, promoting wound healing, and facilitating cell migration. Serpine2, also known as plasminogen activator inhibitor-2 or protease nexin I, is an extracellular serine proteinase inhibitor, which can regulate matrix accumulation and coagulation under pathophysiologic conditions. OPN is a glycosylated phosphoprotein which has been reported to augment natural killer T cell activation, trigger neutrophil infiltration in inflammatory liver diseases, and increase monocyte chemoattractant protein-1 or macrophage inflammatory protein-1β production through the NF-kB and mitogen-activated protein kinase (MAPK) pathways in rheumatoid arthritis. S100A8 belongs to a member of the S100 family of the elongation factor (EF) hand calcium-binding proteins; in inflammatory states, expression of S100A8 is co-upregulated with S100A9 by neutrophils, activated monocytes, and macrophages which act as a chemotactic molecule. BTNL2 has been reported as the first butyrophilin family member that possesses an immunoregulatory function, which inhibits T cell proliferation and regulates T cell activation and tolerance.

The nucleotide sequences of the biomarker genes as described above and the corresponding amino acid sequences of their gene products are well known in the art. For example, the cDNA sequences of human Tmsb4, Serpine2, OPN, BTNL2, S100A8, and CysC are SEQ ID NOS: 1, 3, 5, 7, 9 and 11, respectively, and their corresponding amino acid sequences are SEQ ID NOS: 2, 4, 6, 8, 10 and 12, respectively.

A test sample as used herein includes a variety of sample types obtained from a subject to be diagnosed or prognosed such as a biopsy specimen or tissue cultures or cells derived therefrom. In particular, the test sample is a renal tissue. In one embodiment, the test sample includes a glomerular tissue which may be obtained by any known method in this art e.g. a sieving technique as described in *Nephrol Dial Transplant* 2006; 21: 1794-1802.

A "normal" sample as used herein refers to a variety of sample types such as tissues or cells that are not diseased as defined herein. The term "normal" refers to a state of a cell or tissue in which the cell or tissue that is apparently free of an adverse biological condition when compared to a diseased cell or tissue having that adverse biological condition. For example, a normal sample is tissues or cells obtained from a normal subject (e.g. an individual known to not have IgA nephropathy or a condition or symptom associated with such disease) or taken from an unaffected area of a patient with a disease as defined herein.

In a particular embodiment, the methods of the invention are conducted by analyzing a test sample obtained from a subject in need for the expression level of one or more genes selected from the group consisting of Tmsb4, Serpine 2, OPN, CysC and any combination thereof. Specifically, the test sample can be obtained in a non-invasive way. More specifically, the test sample is urine.

It is understood that the expression level of the one or more genes as described herein in a sample can be determined by any suitable method known in the art.

In one embodiment, the expression level of the one or more genes is determined by measuring mRNA levels of the one or more genes. Assays based on the use of primers or probes that specifically recognize the nucleotide sequences of the genes as described may be used for the measurement, which include but are not limited to reverse transferase-polymerase chain reaction (RT-PCR) and in situ hybridization (ISH), the procedures of which are well known in the art.

Primers or probes can readily be designed and synthesized by one of skill in the art based on the nucleic acid region of interest. It will be appreciated that suitable primers or probes to be used in the invention can be designed using any suitable method in view of the nucleotide sequences of the genes of interest as disclosed in the art. Specific examples of the primers or probes as used in the present invention are given below.

In another embodiment, the expression level of the one or more genes is determined by measuring polypeptide levels of the one or more genes. Assays based on the use of antibodies that specifically recognize the proteins or polypeptides encoded by these genes as described may be used for the measurement, which include but are not limited to immunohistochemistry (IHC), western blotting, or enzyme-linked immunosorbent assay (ELISA), the procedures of which are well known in the art.

Antibodies as used herein may be polyclonal or monoclonal. Polyclonal antibodies directed against a particular protein are prepared by injection of a suitable laboratory animal with an effective amount of the peptide or antigenic component, collecting serum from the animal, and isolating specific sera by any of the known immunoadsorbent techniques. Animals which can readily be used for producing polyclonal antibodies as used in the invention include chickens, mice, rabbits, rats, goats, horses and the like.

In general, the use of monoclonal antibodies in the detection assays of the present invention is preferred because large quantities of antibodies and similar reactivity may be produced. The preparation of hybridoma cell lines for monoclonal antibody production is done by fusing an immortal cell line and the antibody producing lymphocytes. This can be done by techniques which are well known to those who are skilled in the art.

The present invention will now be described more specifically with reference to the following embodiments, which are provided for the purpose of demonstration rather than limitation.

EXAMPLE 1

Establishment of a Prg-IgAN Animal Model and the Clinical and Pathological Evaluation Thereof Prg-IgAN was induced in B-cell-deficient (BCD) mice by daily injection of purified IgA anti-phosphorylcholine and pneumococcal C-polysaccharide (PnC) as described previously (*Kidney Int* 2006; 70: 283-297). To confirm the establishment of the IgAN animal model, clinical and pathological evaluation was conducted as below.

Urine and blood samples were collected from the mice at different time points, which were analyzed for proteinuria and blood urea nitrogen (BUN) and creatinine (Cr) levels by using a urease assay and a picric acid method respectively (*Nephron* 1998; 78: 440-452). BCD mice treated with saline only were used as normal controls.

Figure 1:
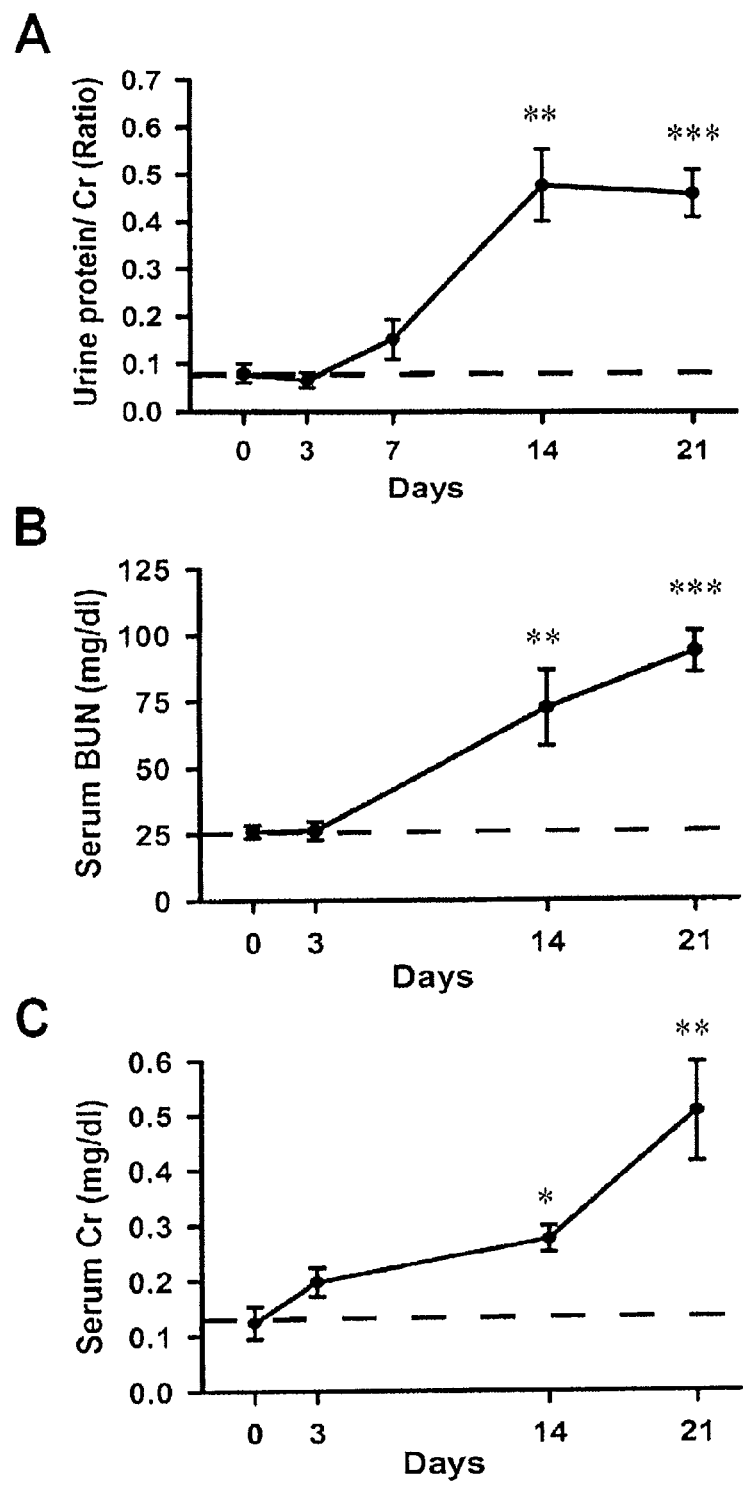
FIG. 1 shows the assessment of proteinuria and renal function of the Prg-IgAN model wherein (A) indicates the urine protein levels, (B) indicates the serum BUN levels, and (C) indicates the serum Cr levels. Each point represents the mean±SE. The dashed line indicates the mean of urine or serum samples from the normal control (day 0). $*p<0.05$ and $**p<0.01$ represent statistical significance compared to the normal control (day 0).

As shown in FIG. 1A, a significant increase of Cr-corrected urine protein levels (0.48±0.07) was observed in the Prg-IgAN mice at day 14 compared with basal levels (0.08±0.02) ($p<0.01$), and the protein levels remained a range of high levels until day 21 when the animals were sacrificed. BUN levels were significantly elevated on day 14 (72.45±14.13 mg/dl compared with basal levels of 25.90±2.34 mg/dl in normal controls; $p<0.01$), showing persistently high levels until day 21 when the mice were sacrificed. Similarly, Cr levels were significantly increased on day 14 compared with basal levels (0.27±0.02 mg/dl vs. 0.12±0.03 mg/dl; p<0.05), and maintained high levels until the mice were sacrificed (FIGS. 1B and C).

In addition, mice were sacrificed at different time points for pathological evaluation as described previously (*Kidney Int* 2006; 70: 283-297). Briefly, renal tissues were fixed in 10% buffered formalin and embedded in paraffin for routine histopathologic evaluation. Sections of the formalin-fixed renal tissue were immersed in xylene to remove paraffin, rehydrated in graded ethanol, stained with hematoxylin and eosin. Scoring of the severity of renal lesions was performed subsequently in which the proportion (percentage) was calculated for the following four major components: (1) proliferation in the glomerular tuft, (2) crescentic-like formation, (3) glomerular sclerosis, and (4) periglomerular inflammation, respectively.

Figure 2:
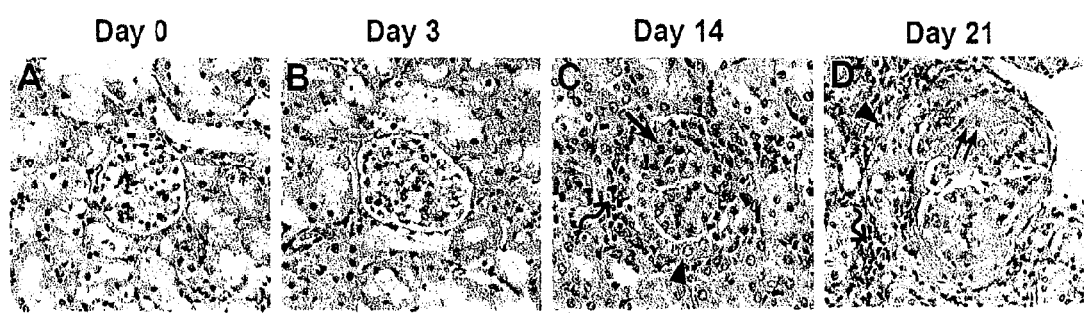
FIG. 2 shows the renal histopathology of the Prg-IgAN model wherein (A) to (D) indicate the progressive changes of glomerular proliferation (arrow), crescentic-like formation (arrowhead), sclerosis (double arrows), and periglomerular inflammation (curved arrow), respectively; and (E) to (H) indicate the scoring of these changes. The results were obtained by haematoxylin and eosin staining. Original magnification is ×400 each. $*p<0.05$ and $**p<0.01$ represent statistical significance compared to normal control (day 0).
Figure 2:
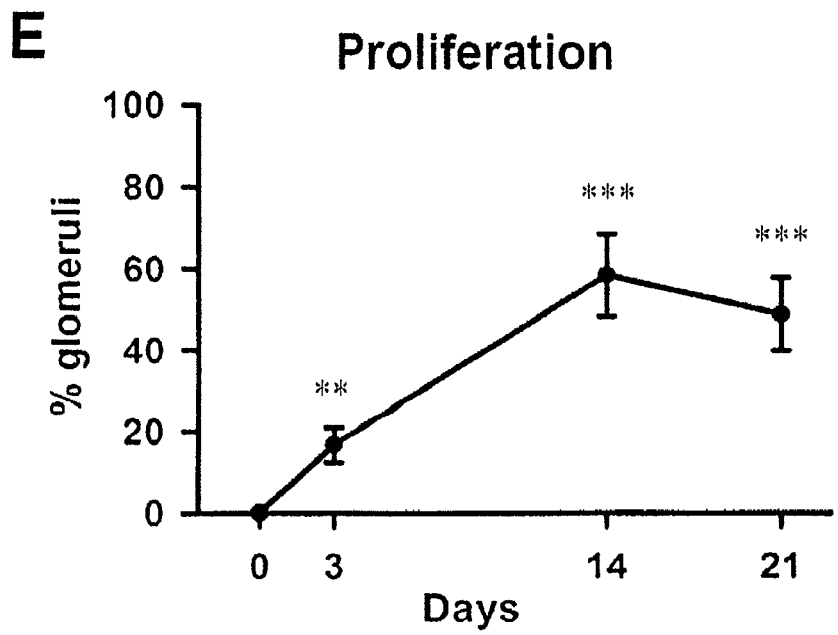
Figure 2:
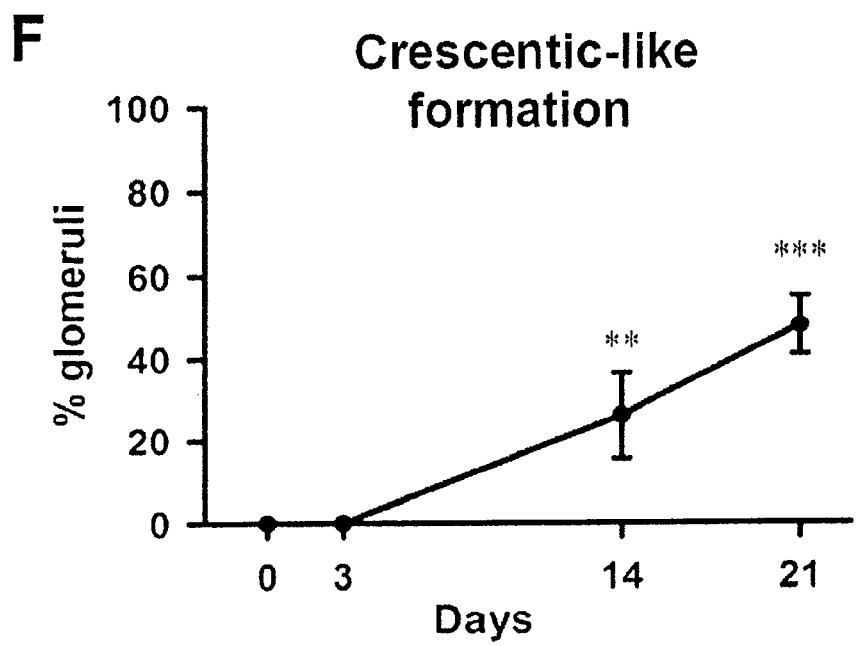
Figure 2:
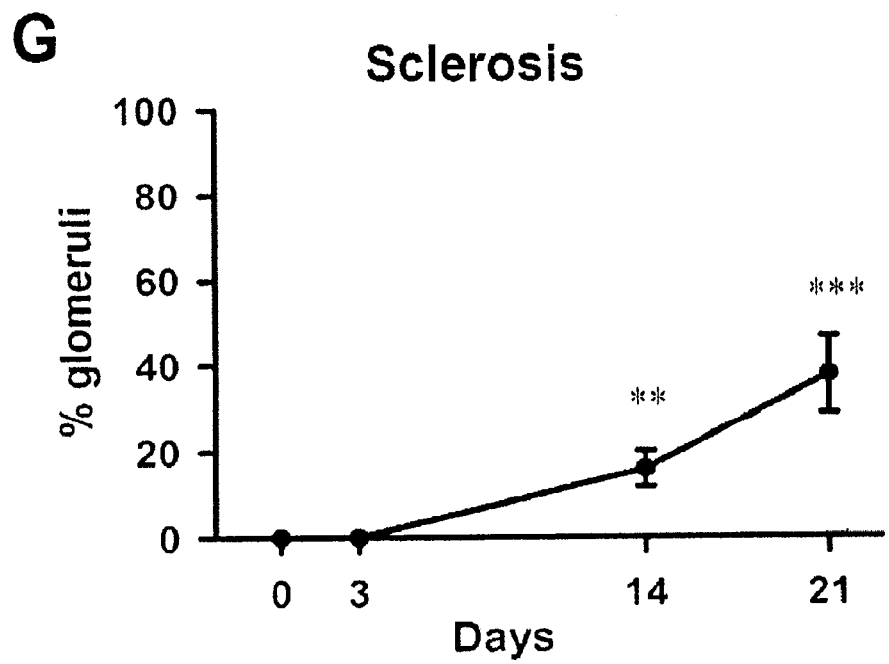
Figure 2:
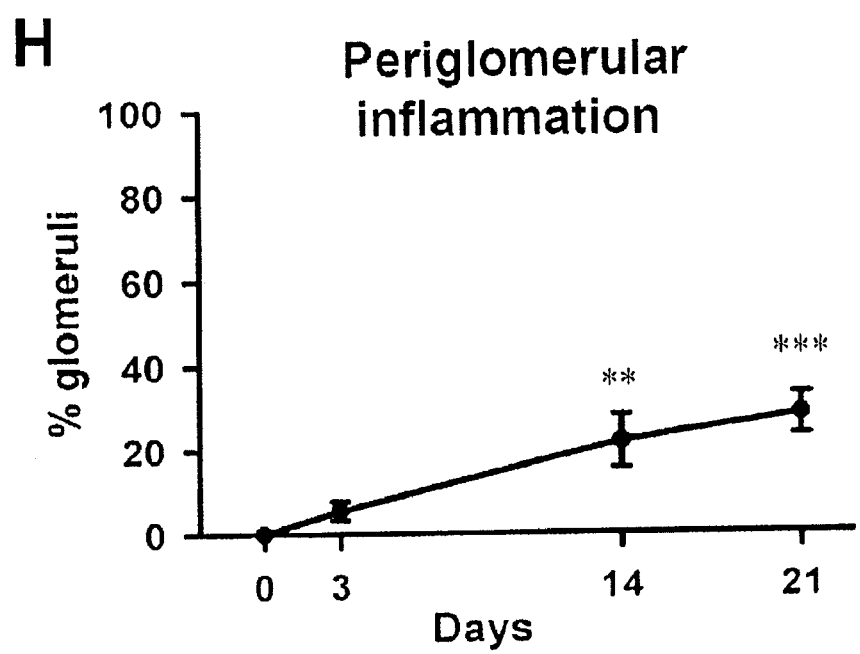

As shown in FIG. 2, as early as day 3 after the induction of disease, the BCD mice that received the administration of IgA and PnC developed diffuse mesangial cell proliferation, which then progressed into crescent-like formation and sclerosis by day 21 compared with normal controls. In addition to the glomerular lesions, various tubulointerstitial changes were also observed at this point, including tubulointerstitial (especially periglomerular) inflammation, tubular atrophy with proteinaceous casts and occasional erythrocyte casts in the tubules, compared with normal controls.

EXAMPLE 2

Gene Expression Profiling

To characterize the profile of altered gene expressions in the glomeruli of the Prg-IgAN model, a combined laser capture microdissection (LCM) and cDNA microassay analysis was conducted. Briefly, LCM was performed to obtain glomerular sections from normal controls and the Prg-IgAN mice at day 21 according to the protocols as previously described (*Reprod Biol Endocrinol* 2007; 5: 18; and *Methods Mol Biol* 2009; 466: 73-82). For each sample, approximately 150 glomeruli were harvested from at least three consecutive sections. Subsequently, cDNA microarray analysis was performed as described previously (*Nephrol Dial Transplant* 2006; 21: 288-298). In total, 8,500 mouse gene spots were screened for the Prg-IgAN model at day 21 versus normal controls.

As a result, totally 918 up-regulation genes (Prg-IgAN at day 21/normal control ratio☐2) in the glomerulus were identified. Highly expressed genes of interest with the ratio☐10 (totally 39 genes), including Tmsb4, Serpine2, OPN, BTNL2, S100A8 and CysC, in the Prg-IgAN model mainly based on the potential correlation between their known biological activities and inflammatory processes were chosen for further verification. These six genes have not been reported elsewhere so far on IgAN for subsequent confirmatory analyses.

EXAMPLE 3 mRNA Expression of Candidate Genes

To determine whether these upregulated genes in the glomerulus were associated with the progression of IgAN, a time-course (days 0, 3, 14, and 21) mRNA expression analysis by RT-PCR was followed in isolated glomeruli from the Prg-IgAN model. The glomeruli samples of the Prg-IgAN mice were isolated with a sieving technique as described previously (*Nephrol Dial Transplant* 2006; 21: 1794-1802), and then subjected to total RNA extraction with Trizol reagent (Life Technologies, Md., USA) according to the manufacturer's instruction. Subsequently, real-time RT-PCR was conducted based on the RNA samples with gene-specific primers as shown in Table 1.

TABLE 1

Primer sequences used for real-time RT-PCR in animal samples

| Gene (mouse) | Primer sequences | |
|---|---|---|
| BTNL2 | 5'-CTCTGGGCCAGGAGAAAAC-3' | SEQ ID NO: 13 |
| | 5'-TGAGCCTCTCATCAGAAGGAA-3' | SEQ ID NO: 14 |
| CysC | 5'-TACAACAAGGGCAGCAACGA-3' | SEQ ID NO: 15 |
| | 5'-GCACCCTTCTGCGAGATGAA-3' | SEQ ID NO: 16 |
| GAPDH | 5'-TCCGCCCCTTCTGCCGATG-3' | SEQ ID NO: 17 |
| | 5'-CACGGAAGGCCATGCCAGTGA-3' | SEQ ID NO: 18 |
| OPN | 5'-CTCGTGCAGGAAGAACAGAAGC-3' | SEQ ID NO: 19 |
| | 5'-GAGTCAAGTCAGCTGGATGAACC-3' | SEQ ID NO: 20 |
| S100A8 | 5'-CCCGTCTTCAAGACATCGTTTG-3' | SEQ ID NO: 21 |
| | 5'-ATATCCAGGGACCCAGCCCTAG-3' | SEQ ID NO: 22 |
| Serpine 2 | 5'-ATGCCTGGGATGCTGGATGC-3' | SEQ ID NO: 23 |
| | 5'-AACCTCTCCTGCCACACTGA-3' | SEQ ID NO: 24 |
| Tmsb4 | 5'-CAGATCAGACTCTCCTCGTT-3' | SEQ ID NO: 25 |
| | 5'-TCTCTGCTAGCCAGACCATC-3' | SEQ ID NO: 26 |

Figure 3:
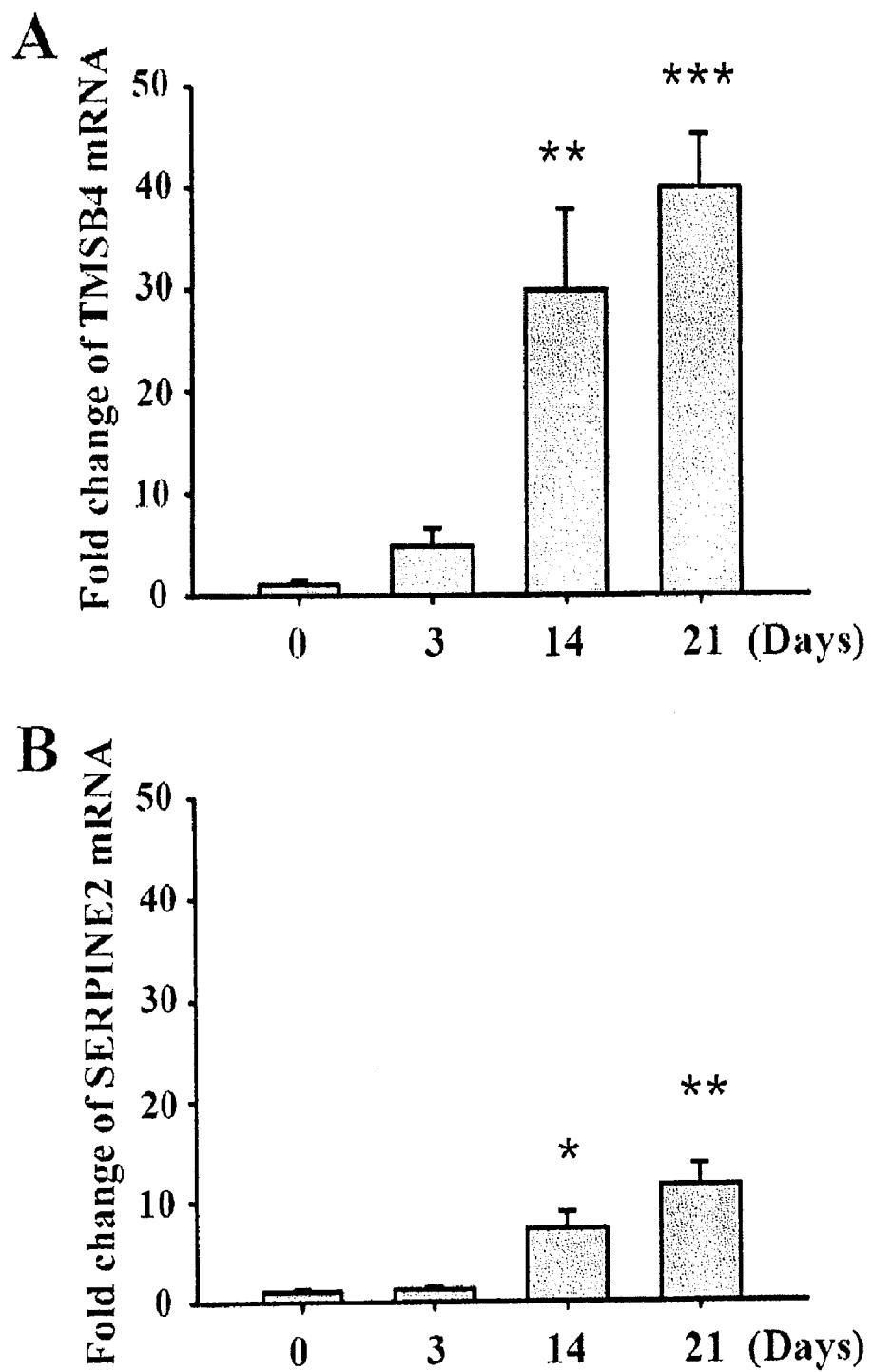
FIG. 3 shows the quantitative analysis of mRNA levels of isolated glomeruli from the Prg-IgAN model by real-time RT-PCR in a time-course manner wherein (A) to (F) indicate the results for Tmsb4, Serpine2, OPN, BTNL2, S100A8, and CysC, respectively. Each point represents the mean±SE. $*p<0.05$, $p<0.01$, and $*p<0.005$ represent statistical significance compared to normal control (day 0).
Figure 3:
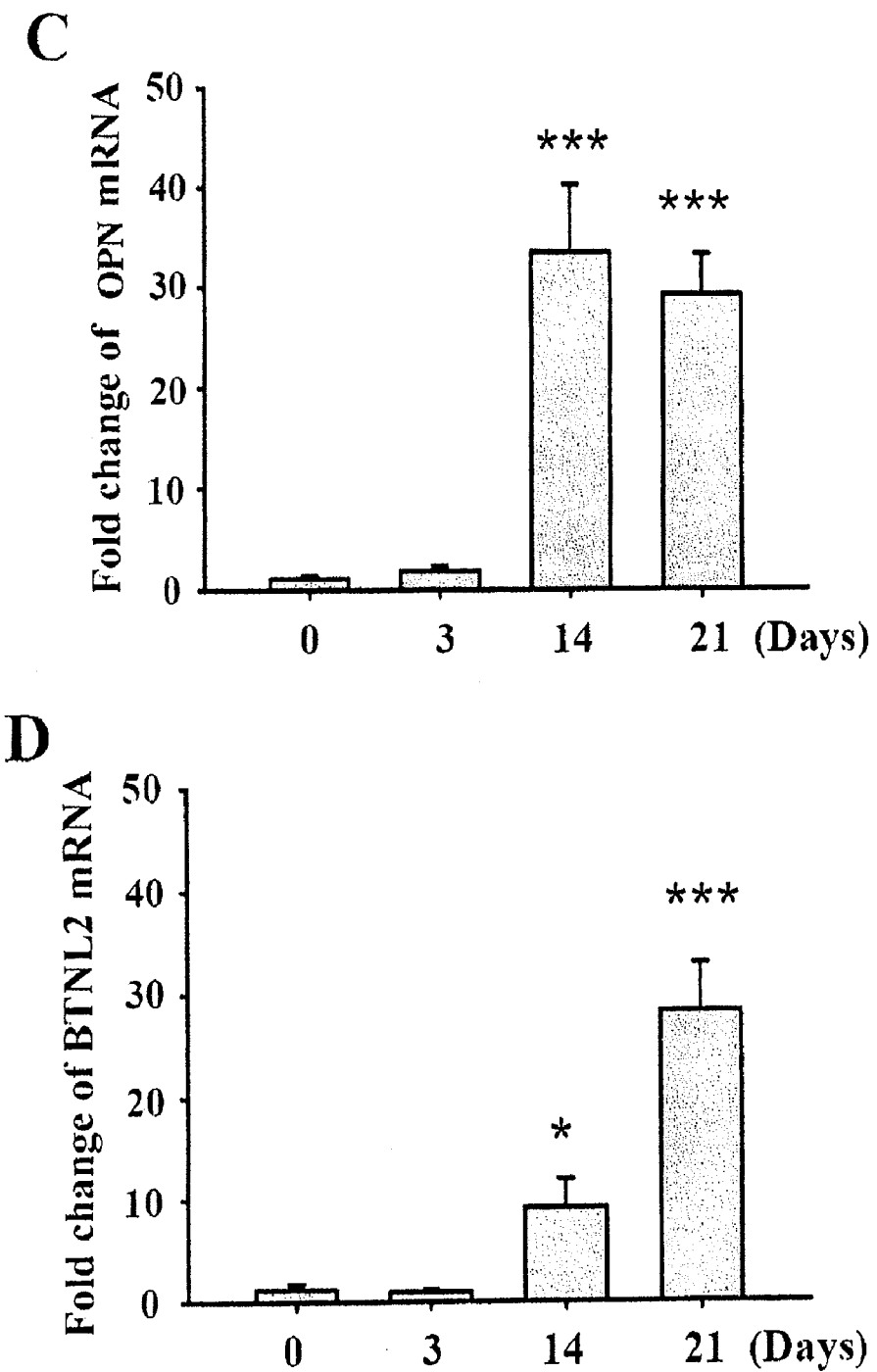
Figure 3:
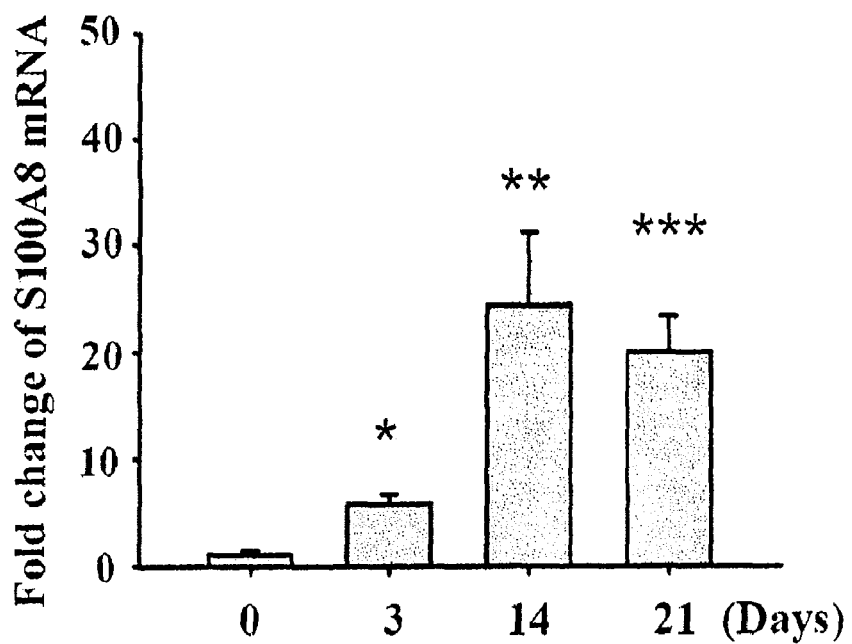
Figure 3:
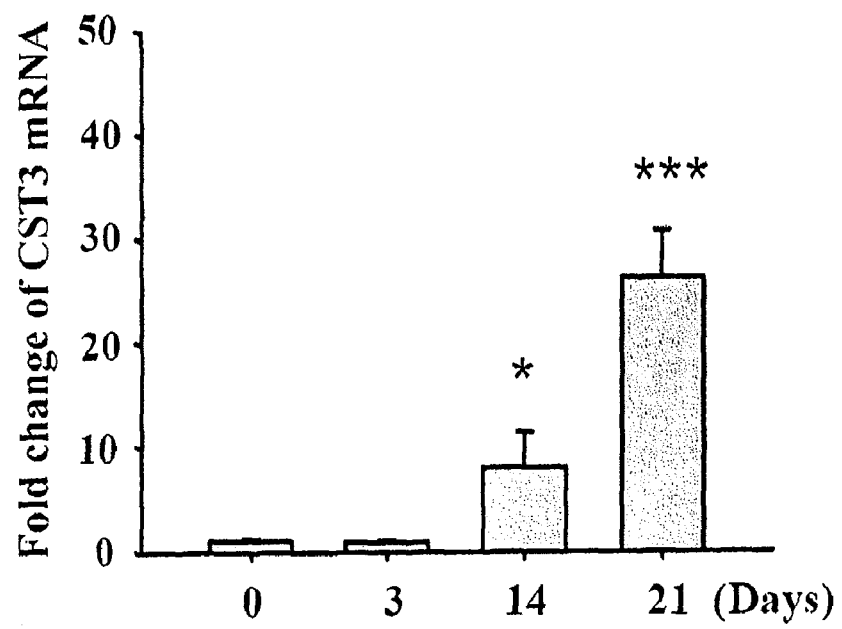

FIG. 3 shows the quantitative results of RT-PCR with normalization to GAPDH. As shown in the results, there was a significantly increased mRNA expression of these genes in the glomeruli of the Prg-IgAN model at day 3 (S100A8, 5.82±0.91-fold, p<0.05), day 14 (Tmsb4, 29.94±7.94-fold, p<0.01; Serpine2, 7.21±1.69-fold, p<0.05; OPN, 33.61±6.77-fold, p<0.005; BTNL2, 9.21±2.78-fold, p<0.05; S100A8, 24.58±6.82-fold, p<0.01; CysC, 8.05±3.35-fold, p<0.05), and at day 21 (Tmsb4, 40.07±5.23-fold, p<0.005; Serpine2, 11.59±2.11-fold, p<0.01; OPN, 29.41±4.03-fold, p<0.005; BTNL2, 28.33±4.67-fold, p<0.005; S100A8, 20.21±3.35-fold, p<0.005; CysC, 26.22±4.55-fold, p<0.005) compared to normal controls.

EXAMPLE 4

Cellular Localization of RNA or Encoded Proteins of the Candidate Genes in the Kidney For assessing the cellular source of the expression of the particular genes in renal tissues from the Prg-IgAN mice, ISH and IHC were performed in a time-course manner.

1. ISH

For ISH, cDNA probes for Tmsb4, Serpine2, OPN, BTNL2, S100A8, and CysC were generated in mouse kidney by RT-PCR with primers as set forth in Table 1 and then labeled with digoxigenin. The sequences of the cDNA probes as prepared are shown in Table 2.

TABLE 2

Probe sequences for ISH in animal samples

| Gene (mouse) | Probe sequences |
|---|---|
| BTNL2 | 5'-ATCTGAGCCTCTCATCAGAAGGAAGTCGCCGCCTGTG GTTTTCGTCATTCTTGTTATTTTCCTGATTGCTGCTGTGT GTTTGTTCATTGGTCCGCCGCCACCGTTTCACCTTGATCA GGTCGATAGCCATGGCCAGAGGCAGCACCACAACAGGCAG GGTCATCCATAGCAAAGCTATCTTGGAGTCTGAGAGAGGG AAACGGGCTGTTTTCTCCTGGCCCAG-3 (SEQ ID NO: 27) |

TABLE 2-continued

Probe sequences for ISH in animal samples

| Gene (mouse) | Probe sequences |
|---|---|
| CysC | 5'-GCACCCTTCTGCGAGATGAAACACTATAGGGAAGGAG CACAAGTAAGGAACAGTCTGCATGATCCTTCTAGACTCAG CCCTTAGGCATTTTTGCAGCTGAATTTTGTCAGGGAGTGT GTGCCTTTCCAGGGCACGCTGTAGATCTGGAAGGAGCAGA GTGCCTTCCTCATCAGATGGGGCTGGTCATGGAAAGGACA GTCAGTCAAATTTGTCTGGGACTTGGTACATGTAGTTCGG CCCATCTCCACATCCAAAAAATAGTTCACTCCAGCCACGA GCTGCTTACGAGCTCTCACCACCTGTATGGCGCGGCTGTG GTACGCATCGTTGCTGCCCTTGTTGTA-3' (SEQ ID NO: 28) |
| OPN | 5'-CAGAAGCTTTTGGTTACAACGGTGTTTGCATGAAACA ACAGACTAAGCTAAGAGCCCAAAATATTACCTCTCTTTCT CTACATACATATATCCACTGAACTGAGAAATGAGCAGTTA GTATTCCTGCTTAACCCTCACTAACACTTTTTCTTGTTTT TACTAAATGCAAAGTAAGGAACTGTGTTTTTGCCTCTTCT TTAGTTGACCTCAGAAGATGAACTCTCTAATTCATGAGAA ATTCGGAATTTCAGATACCTATCATCTTCCTTACTCTTAG GGTCTAGGACTAGCTTGTCCTTGTGGCTGTGAAACTTGTG GCTCTGATGTTCCAGGCTGGCTTTGGAACTTGCTTGACTA TCGATCACATCCGACTGATCGGCACTCTCCTGGCTCTCTT TGGAATGCTCAAGTCTGTGTGTTTCCAGACTTGGTTCATC CAGCTGACTTGACTC-3' (SEQ ID NO: 29) |
| S100A8 | 5'-ATATCCAGGGACCCAGCCCTAGGCCAGAAGCTCTGCT ACTCCTTGTGGCTGTCTTTGTGAGATGCCACACCCACTTT TATCACCATCGCAAGGAACTCCTCGAAGTTAATTGCATTG TCACTATTGATGTCCAATTCTCTGAACAAGTTTTCGATAT TTATATTCTGCACAAACTGAGGACACTCAGTAGTGACCAT TTTCTTGAAGTCATTCTTGTAGAGGGCATGGTGATTTCCT TGTATATTGGAATAATTGTGGTAGACATCAATGAGGTTGC TCAAGGCCTTCTCCAGTTCAGACGGCATTGTCACGAAAGA TTTCCTTTCAAACGATGTCTTGAAGACGGG-3' (SEQ ID NO: 30) |
| Serpine 2 | 5'-AACCTCTCCTGCCACACTGATTAATCCTCTCCTGGAA AGTCACACATATCAACAGGAATGAAACAAAGATGCTGAAC TTGACAGACAGCAAATACTCGAGAGGGTTGTTAACCTAGA TAACTGATCAGTAGTTTAAAGAAATCTTCTAGACATCGTG AAACCGGCCTGCTCATCCTTCACTACAGCATCCCAGGCAT CCAGCATCCCAGGCAT-3' (SEQ ID NO: 31) |
| Tmsb4 | 5'-TCTCTGCTAGCCAGACCATCAGATGGGTGGGAGAGGC AGGGGAGGCCTTCCTGCTCAGTAGTTCTGATTCTTTGATG TGAAAGGGGCAGCACAGTCATTTAAACTTGATCCAACCTC TTTGCATCTTACAAAGTTAAACAGCTAAAAGAAGTAAAAT AAGAAGGCAATGCTCGTGGAATGTACAGTGCATATTGGCG GCGCTCGCCTCATTACGATTCGCCAGCTTGCTTCTCTTGT TCAATTGTTTCTTTTGAAGGCAGAGGATTTTTCTCTTGCG TTTCTGTTTTCTTCAACTTCGACTTATCGAATTTCTCGAT CTCAGCCATATCGGGTTTGTCAGACATGGTTGCTGGAAGG AGCCGAGCGAGCTGCGCGAACGAGGAGAGTCTGATCTG-3' (SEQ ID NO: 32) |

Renal tissues were obtained from Prg-IgAN mice and then subjected to ISH with the aforementioned probes according to the protocols as described previously (*J Biol Chem* 2006; 281: 1066-1072).

Figure 4:
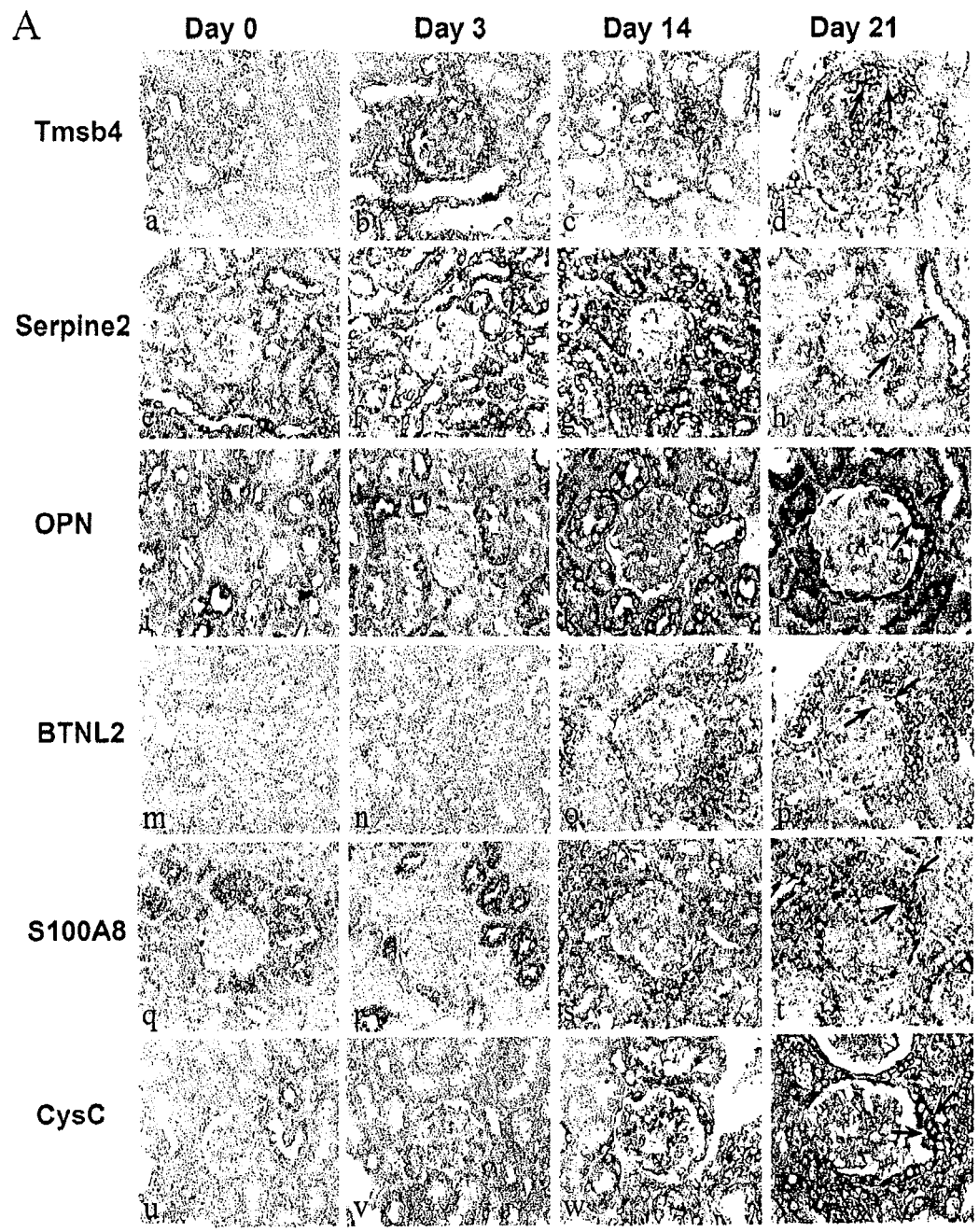
FIG. 4 shows the renal in situ hybridization (ISH) results of the Prg-IgAN model in a time-course manner, wherein (A) represents the kidney sections from the normal control (day 0) and the IgAN model (day 3, day 14, and day 21) for Tmsb4, Serpine2, OPN, BTNL2, S100A8, and CysC. Positive cells were stained in deep brown. Arrows in (d), (h), (l), (p), (t), and (x) indicate epithelial cells in crescent-like formation of the glomerulus. Original magnification is ×400 each. Semi-quantitative analysis of cellular protein expression by IHC was showed in (B) to (G). The scoring was performed for the three major components: parietal epithelial cells (solid bars), podocytes (open bars) and mesangial cells (hatched bars). Each bar represents the mean±SE. $*p<0.05$, $p<0.01$, and $*p<0.005$ represent statistical significance compared to the normal control (day 0). The symbol "#" means data not detectable.
Figure 4:
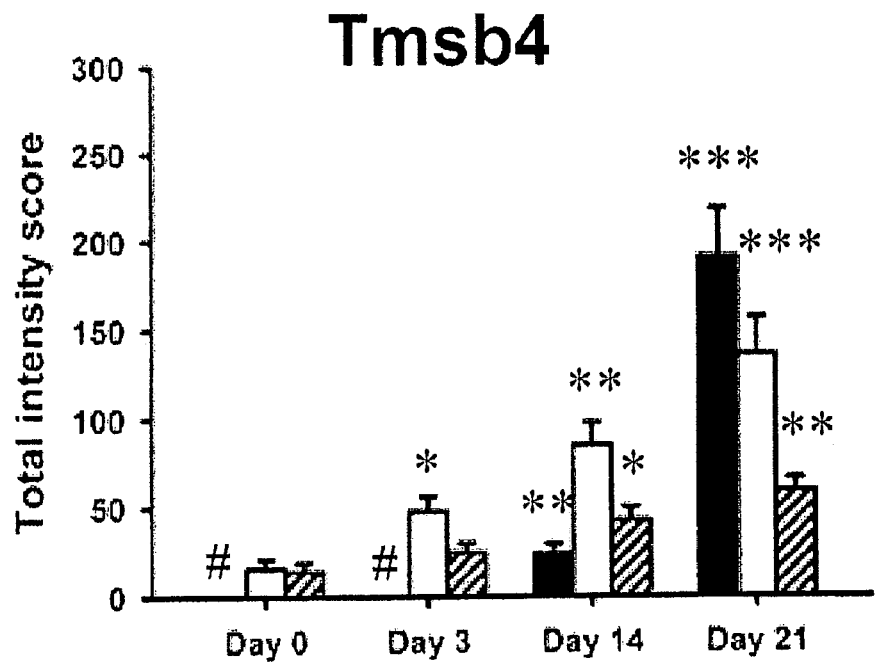
Figure 4:
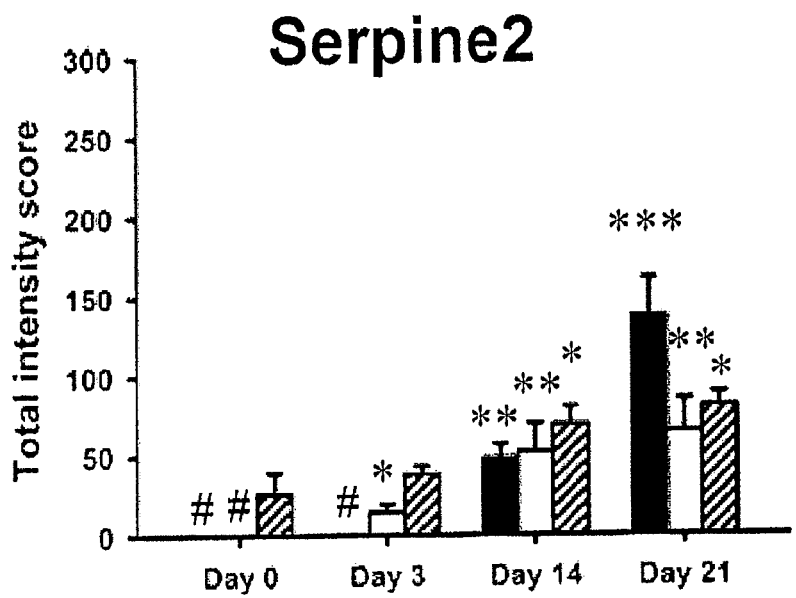
Figure 4:
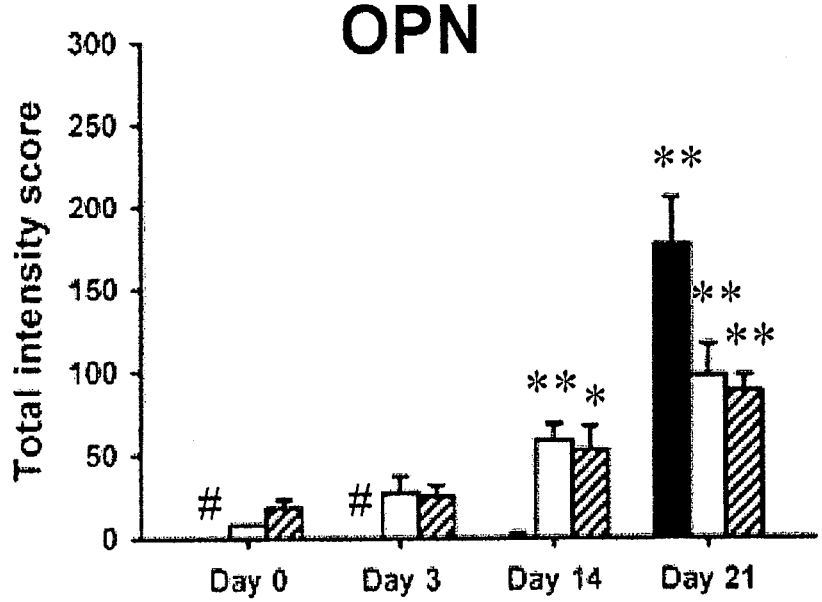
Figure 4:
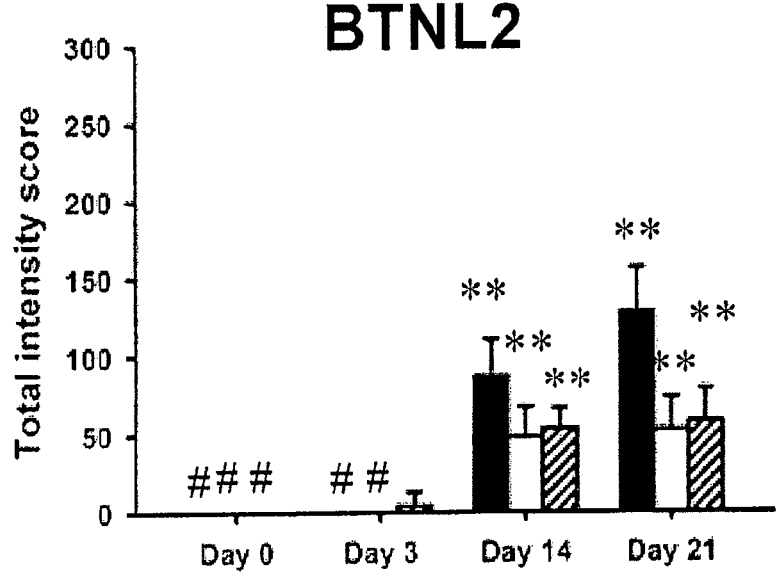
Figure 4:
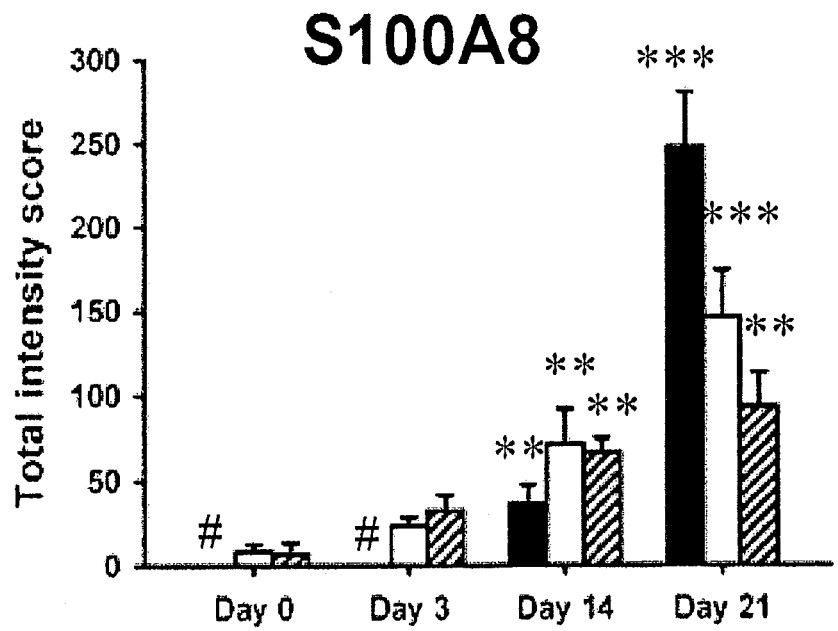
Figure 4:
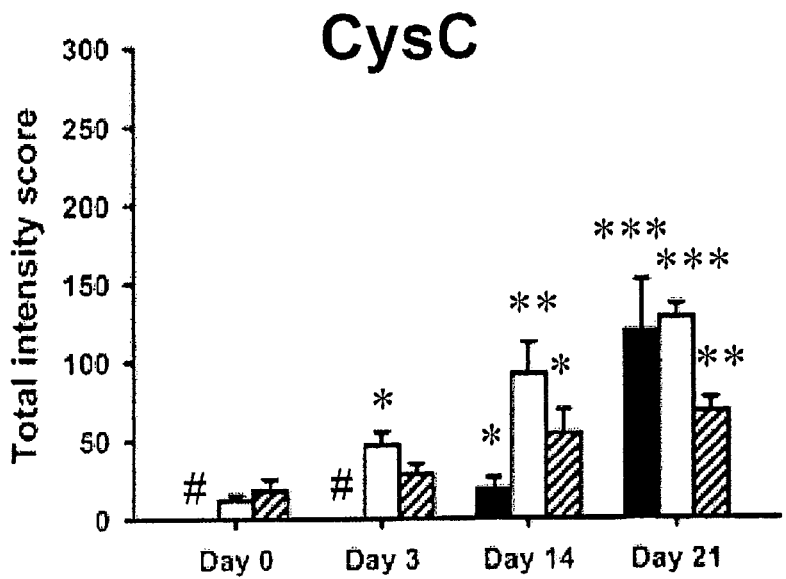

As shown in FIG. 4A, time-dependent enhancement in mRNA expression levels were observed for all the Tmsb4, Serpine2, OPN, BTNL2, S100A8, and CysC mainly in the glomerulus of the Prg-IgAN model although some renal tubules were found to have expressed these genes as well. Of note, at day 21, when glomerular crescent-like formation or sclerosis became outward, the Prg-IgAN mice were found to have the most extensive and intensive mRNA expression of all these genes, compared with those of earlier stages of the Prg-IgAN mice and normal controls (FIG. 4B-G). Besides, enhanced mRNA expression of BTNL2 and S100A8 was also identified in inflammatory cells infiltrating around glomerulus of the Prg-IgAN mice, as demonstrated by ISH (FIG. 4A, p and t).

2. IHC

Paraffin-embedded sections of the Prg-IgAN mice was obtained as described previously (*J Am Soc Nephrol* 2007; 18: 1777-1788), and then subjected to IHC with specific antibodies including anti-Tmsb4, anti-Serpine2, anti-S100A8 (Santa Cruz Biotechnology, Calif., USA), anti-mouse OPN (Assay Designs Inc., Mich., USA), anti-human OPN (Lab Vision Corp., Calif., USA), anti-CysC (Upstate, N.Y., USA).

Figure 5:
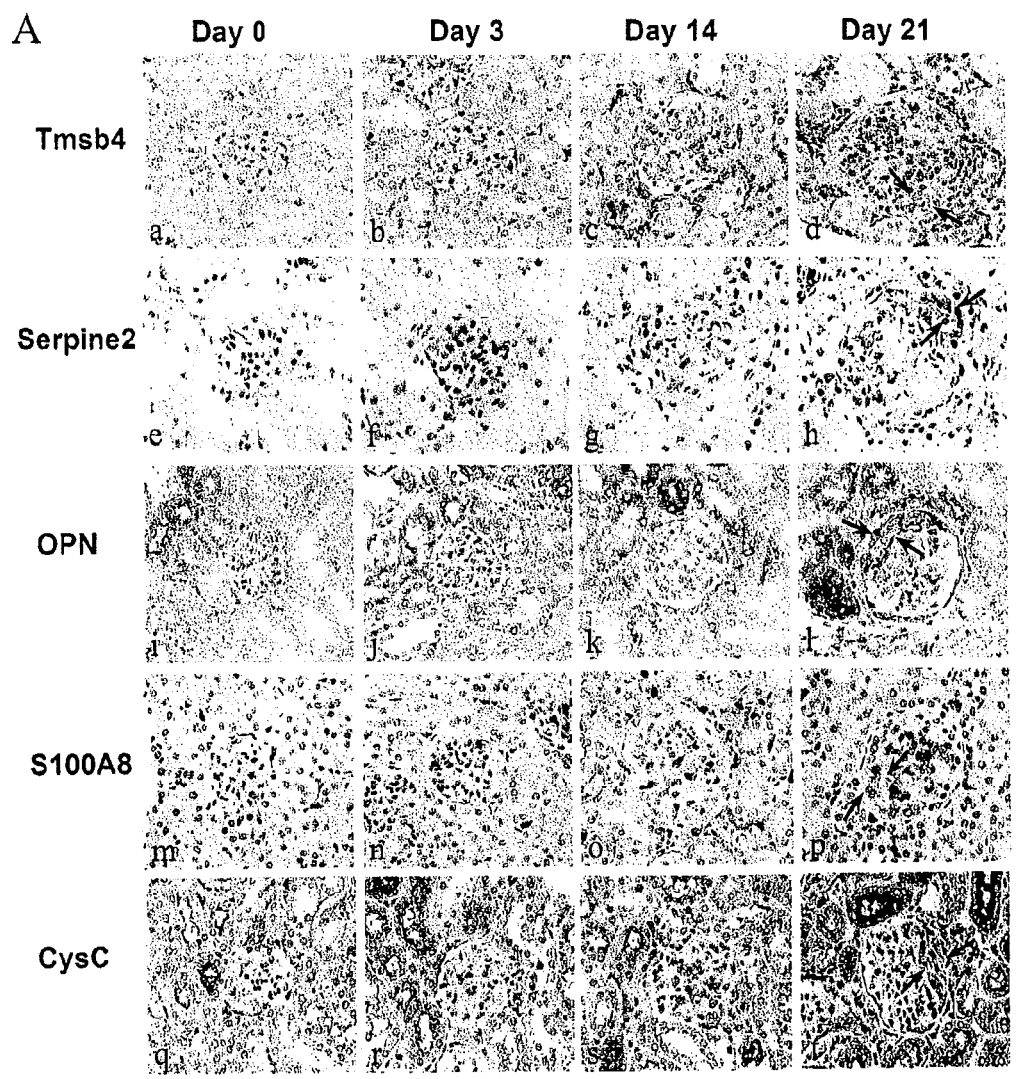
FIG. 5 shows the renal immunohistochemistry (IHC) results of the Prg-IgAN model in a time-course manner wherein (A) represents the kidney sections from the normal control (day 0) and the IgAN model (day 3, day 14, and day 21) for Tmsb4, Serpine2, OPN, S100A8 and CysC. Positive cells were stained in red. Arrows in (d), (h), (l), (p), and (t) indicate epithelial cells in crescent-like formation of the glomerulus. Original magnification is ×400 each. Semi-quantitative analysis of cellular protein expression by IHC was showed in (B) to (F). The scoring was performed for the three major components: parietal epithelial cells (solid bars), podocytes (open bars) and mesangial cells (hatched bars). Each bar represents the mean±SE. $*p<0.05$, $**p<0.01$.
Figure 5:
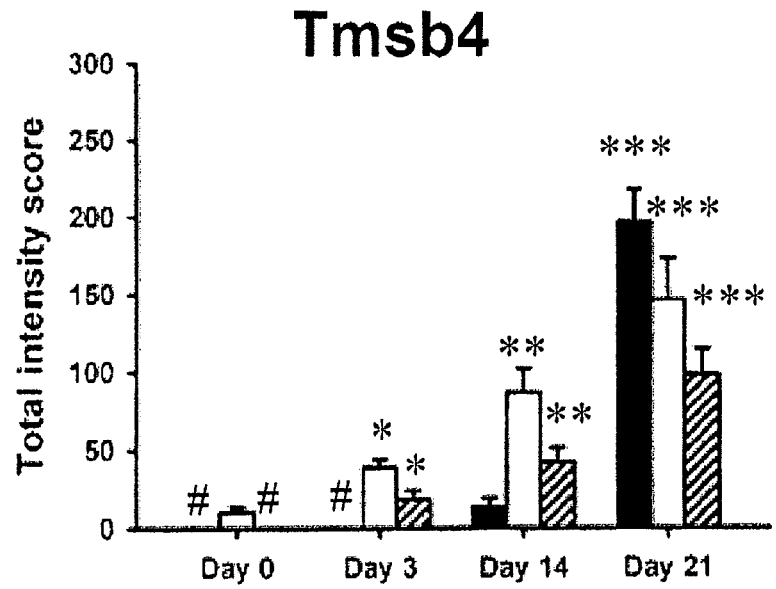
Figure 5:
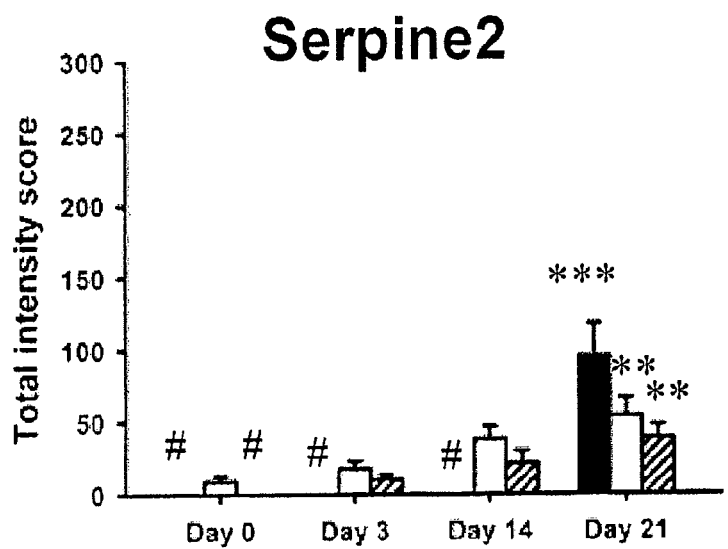
Figure 5:
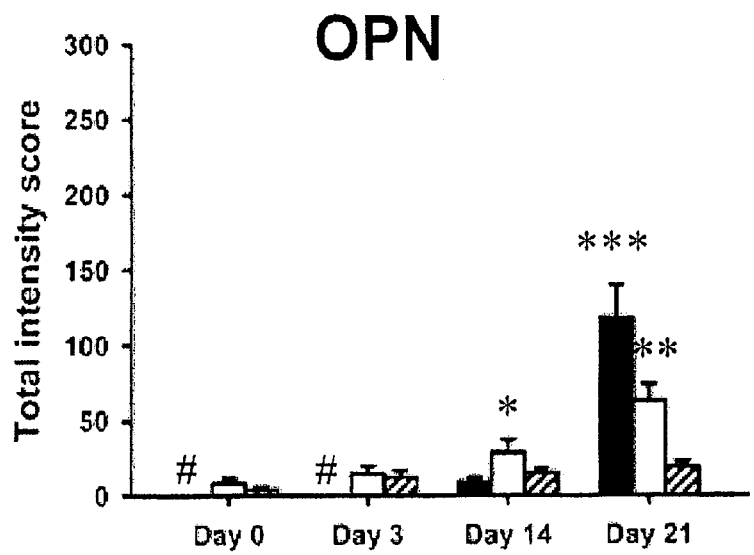
Figure 5:
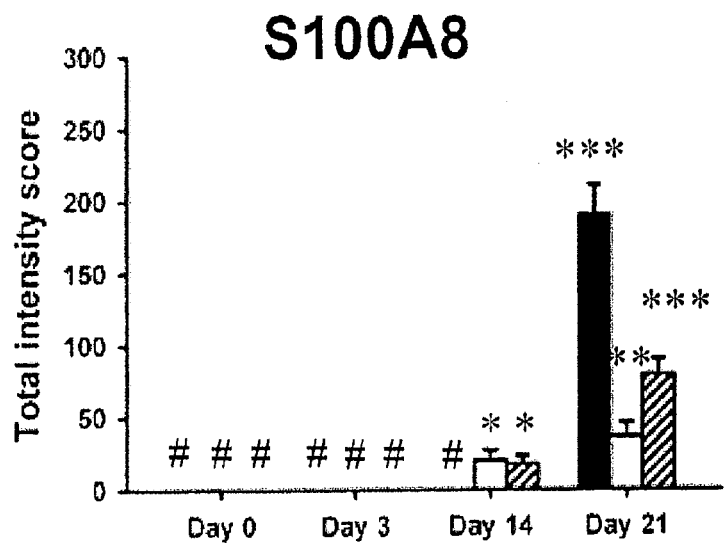
Figure 5:
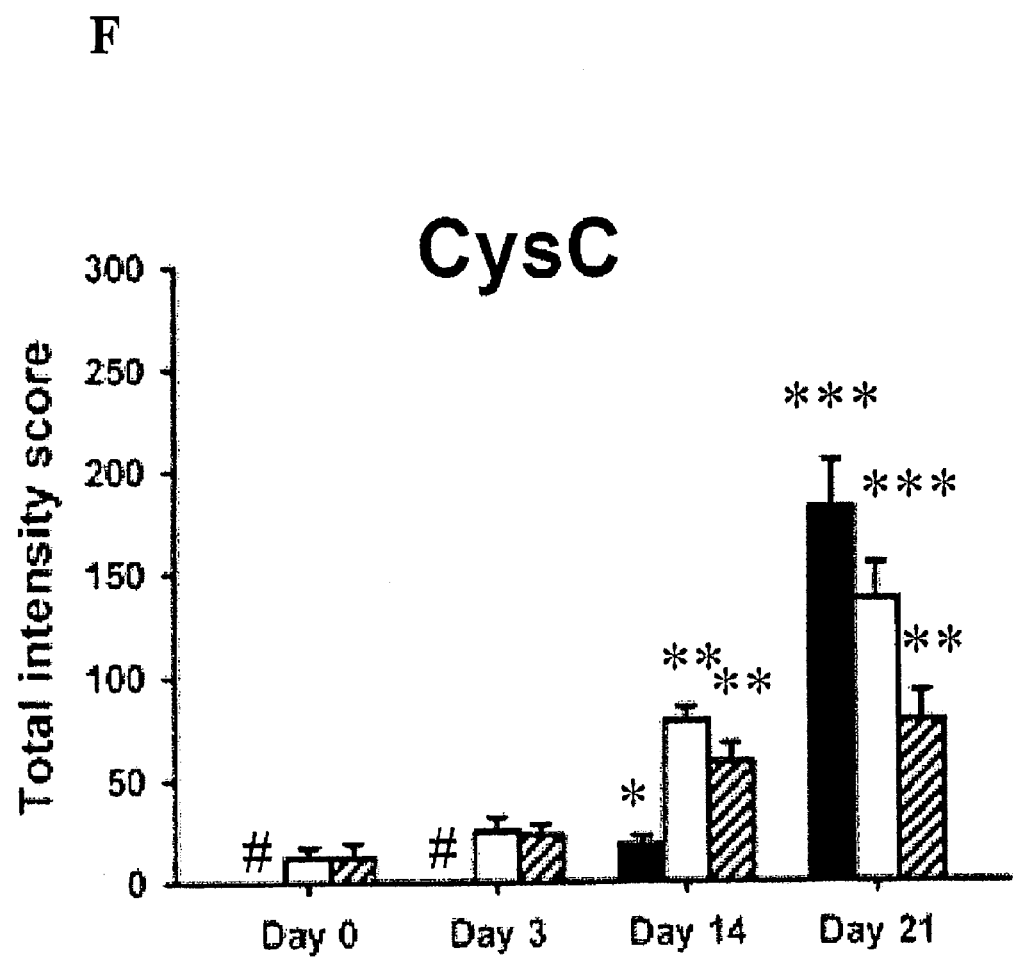

As shown in FIG. 5, the pattern of expression of Tmsb4, Serpine2, OPN, S100A8, and CysC proteins (FIG. 5) was generally similar to that of ISH as described above. There was no specific antibody available for BTNL2 at present. Renal tubular epithelial cells showed CysC protein in a particular pattern that suggests reabsorption of the protein instead of the production of the protein.

EXAMPLE 5

Increased Protein Levels of Candidate Genes in Urine Samples of Animals

Next, we wanted to identify whether these Prg-IgAN model-associated proteins were excreted in urine. Urine samples were collected from the Prg-IgAN mice at different time points and protein levels of individual proteins of interest in the urine samples were detected by Western blot analysis or ELISA as described previously (*Nephrol Dial Transplant* 2006; 21: 288-298; *BJU Int* 2009). Data were presented as the ratio of the density of each target protein to the Cr concentration of urine as described previously.

As shown in FIG. 6, OPN (1356.47±181.32 vs. 0), CysC (1164.82±268.61 vs. 367.83±73.47), and Serpine2 (1149.35±102.34 vs. 0) proteins were all detectable and significantly increased in urine samples of the Prg-IgAN model at day 21 compared with normal controls (each $p<0.005$), as demonstrated by Western blot analysis. Among them, urine protein levels of Serpine2 were detectable as early as day 7 and were significantly elevated in a time-dependent manner in the Prg-IgAN model, suggesting that Serpine 2 may serve as an early biomarker associated with the development and/or progression of IgAN in a non-invasive approach. There was no detectable urine S100A8 protein in the Prg-IgAN mice or normal controls. No specific antibody was available for the detection of urine Tmsb4 in mice at the present time.

EXAMPLE 6

Upregulated Expression of Candidate Genes Potentially Involved in Enhancement of Apoptosis in Animals We further performed TUNEL in a time-dependent manner to characterize the Prg-IgAN model. Paraffin-embedded sections were stained with an ApopTag Plus Peroxidase in Situ Apoptosis Detection kit (Chemicon, Calif., USA) according to the manufacturer's instructions. The number of apoptotic cells in the glomerulus was counted by calculating positive cells per glomerular cross-section as described previously.

As shown in FIG. 7, quantitative analysis of cell death revealed that glomeruli contained one or more apoptotic nuclei at day 3 (2.40±0.38 cells/gcs), the number of apoptotic nuclei gradually increasing throughout the course of the Prg-IgAN model, and then abruptly increasing at day 21 when the mice were sacrificed, compared to normal control mice (11.52±2.31 cells/gcs vs. 0, $p<0.01$).

EXAMPLE 7

Enhanced Expression of Candidate Genes in Renal Tissues Obtained from IgAN Patients with Unfavorable Factors (UPF)

1. Patient Population

Totally seven IgAN patients with UPF as defined previously (Kidney Int 2007; 71: 343-348) were recruited in the study to verify the expression of the potential biomarker candidates obtained by using the Prg-IgAN model in mice as described above. In addition to both hematuria and proteinuria, renal biopsies of these patients showed moderate hypercellularity, glomerulosclerosis, tubulointerstitial inflammation, and a diffuse glomerular co-deposition of IgG and/or IgM as well as C3. These patients were followed at the Tri-Service General Hospital, Taipei, Taiwan, and all the patients who contributed samples signed their informed consent forms according to the regulations by the Institutional Review Board (IRB) of Tri-Service General Hospital, National Defense Medical Center, Taipei, Taiwan.

Renal tissues and urine samples from the patients were obtained at the time of diagnosis. Renal tissues taken from the unaffected pole of kidneys removed for renal cell carcinoma were used a normal controls. Normal urine samples were collected from apparently healthy volunteers.

2. Gene Expression Assessed by ISH cDNA for Tmsb4, Serpine2, OPN, BTNL2, S100A8, and CysC were generated in human renal biopsy individually by RT-PCR with primers as set forth in Table 3.

TABLE 3

Primer sequences for real-time RT-PCR in human samples

| Gene (human) | Primer sequences | | |
|---|---|---|---|
| BTNL2 | 5'-GAGGTGACTGAGATGCAGATGG-3' | SEQ ID NO: | 33 |
|  | 5'-GGAGGGCTGGATGTTGTGTA-3' | SEQ ID NO: | 34 |
| CysC | 5'-CCAGCAACGACATGTACCAC-3' | SEQ ID NO: | 35 |
|  | 5'-ACAGGTGGATTTCGACAAGG-3' | SEQ ID NO: | 36 |
| OPN | 5'-ACAGCCAGGACTCCATTGAC-3' | SEQ ID NO: | 37 |
|  | 5'-ACACTATCACCTCGGCCATC-3' | SEQ ID NO: | 38 |
| S100A8 | 5'-ATGCCGTCTACAGGGATGAC-3' | SEQ ID NO: | 39 |
|  | 5'-ACGCCCATCTTTATCACCAG-3' | SEQ ID NO: | 40 |
| Serpine 2 | 5'-CTTTGAGGATCCAGCCTCTG-3' | SEQ ID NO: | 41 |
|  | 5'-TGCGTTTCTTTGTGTTCTCG-3' | SEQ ID NO: | 42 |
| Tmsb4 | 5'-ATTCCACAAGCATTGCCTTC-3' | SEQ ID NO: | 43 |
|  | 5'-ACCCCACTTCTTCCTTCACC-3' | SEQ ID NO: | 44 |

These cDNAs fragments as produced were then labeled with digoxigenin as probes for ISH, the sequences of which are shown in Table 4.

TABLE 4

Probe sequences for ISH in human samples

| Gene (human) | Probe sequences |
|---|---|
| BTNL2 | 5'-GGAGGGCTGGATGTTGTGTATCTTCAGTGCCACATTTC CCTTTGCAATGCCATTCTCTATCCACTCTACCCAGCCTCTG TACTCCTCCATCTGCATCTCAGTCACCTC-3' (SEQ ID NO: 45) |
| CysC | 5'-ACAGGTGGATTTCGACAAGGTCATTGTGCCCTGCCAAG GCACAGCGTAGATCTGGAAAGAGCAGAATGCTTTCCTTTTC AGATGTGGCTGGTCATGGAAGGGGCAGTTGTCCAAGTTGGG CTGGGTCTTGGTACACGTGGTTCGGCCCAGCTCCACGTCCA AGAAGTAGTTCACCCCAGCTACGATCTGCTTGCGGGCGCGC ACCACCTGCAGCGCGCGGCTGTGGTACATGTCGTTGCTG-3' (SEQ ID NO: 46) |
| OPN | 5'-CACACTATCACCTCGGCCATCATATGTGTCTACTGTGG GGACAACTGGAGTGAAAACTTCGGTTGCTGGCAGGTCCGTG GGAAAATCAGTGACCAGTTCATCAGATTCATCAGAATGGTG AGACTCATCAGACTGGTGAGAATCATCAGTGTCATCTACAT CATCAGAGTCGTTCGAGTCAATGGAGTCCTGGCTGT-3' (SEQ ID NO: 47) |
| S100A8 | 5'-CACGCCCATCTTTATCACCAGAATGAGGAACTCCTGGA AGTTAACTGCACCATCAGTGTTGATATCCAACTCTTTGAAC CAGACGTCTGCACCCTTTTTCCTGATATACTGAGGACACTC GGTCTCTAGCAATTTCTTCAGGTCATCCCTGTAGACGGCAT-3' (SEQ ID NO: 48) |
| Serpine 2 | 5'-TGCCACGAAAGTGCGTTTCTTTGTGTTCTCGGGTTGGA ACCGTGATTTCCACAGACCCTTGAAATACACTGCGTTGACG AGGACCAGTCTGGTGAGCACACCATCAATAAGATCTGGGGA CAGCAGATTGTCAATCATATCCCTGGTTTCATTTTTAACCC ATGCATTGATGGAATCACAGGCAGAGGCTGGATCCTCAAAG-3' (SEQ ID NO: 49) |
| Tmsb4 | 5'-CACCCCACTTCTTCCTTCACCAACATGCAAGTTCTTTC CTTCCCTGCCAGCCAGATAGATAGACAGATGGGAAAGGCAG GCGCGGCCTTCGTTGTCAGTAGTTCTTTGATGTGAAAGGGG CAGCACAGTCATTTAAACTTGATCCAACCTCTTTGCATCTT ACAAAGTTAAACAGCTAAAAGAAGTAAAATAAGAAGGCAAT GCTTGTGGAAT-3' (SEQ ID NO: 50) |

Renal tissues were obtained from the patients as above-described and subjected to ISH with the aforementioned probes according to the protocols as described previously. FIG. 8 shows the ISH results for the patients.

3. Gene Expression Assessed by IHC

Similar to Example 4, paraffin-embedded sections from the patients were obtained and subjected to IHC with specific antibodies including anti-Tmsb4, anti-Serpine2, anti-S100A8 (Santa Cruz Biotechnology, Calif., USA), anti-mouse OPN (Assay Designs Inc., Mich., USA), anti-human OPN (Lab Vision Corp., Calif., USA), anti-CysC (Upstate, N.Y., USA). FIG. 9 shows the IHC results for the patients.

4. Gene Expression Assessed by Western Blot or ELISA

To determine whether these proteins can serve as biomarkers for non-invasive diagnosis and prognostic prediction of the patients, we further detected urine protein levels in patients using Western blot analysis or ELISA. Urine samples obtained from healthy volunteers served as normal control. As shown in FIGS. 10(A), (B) and (C), urinary protein levels of Serpine2 (525.87±58.68 vs. 0, $p<0.005$), OPN (1748.35±215.99 vs. 0, $p<0.005$), and CysC (1297.86±371.65 vs. 25.66±22.34, $p<0.05$) were significantly increased in the patients compared to the normal controls, as demonstrated by Western blot analysis. By ELISA, urinary levels of Tmsb4 of the IgAN patients with UPF were also significantly increased compared to those of normal controls (0.154±0.024 vs. 0.027±0.006, $p<0.005$) (see FIG. 10(D)). There were no detectable levels of S100A8 in urine from the patients.

The aforementioned results of the gene expression assessed by ISH, IHC, western blot and ELISA are summarized in Table 5.

TABLE 5

Summary of cellular location and urine levels of candidate genes in the IgAN patients with UPF

| | Cellular localization | | | | | | | | | | | Urine levels | |
|---|---|---|---|---|---|---|---|---|---|---|---|---|---|
| | ISH | | | | | | IHC | | | | | Western blot analysis or ELISA | |
| | Normal | | | IgAN | | | Normal | | | IgAN | | | |
| | PEC | P | MC | PEC | P | MC | PEC | P | MC | PEC | P | MC | Normal | IgAN |
| Tmsb4 | trace | + | + | +++*** | +++** | ++* | − | + | trace | +++*** | +++** | ++* | trace | +*** |
| Serpine2 | trace | trace | trace | +++** | ++** | ++** | trace | trace | − | +** | +* | +** | − | +*** |
| OPN | − | trace | + | +++*** | ++* | ++** | trace | trace | trace | +++** | +* | ++** | − | +*** |
| BTNL2 | trace | trace | trace | +++** | +* | ++** | ND | ND | ND | ND | ND | ND | ND | ND |
| S100A8 | trace | − | trace | +++** | +* | ++* | trace | trace | trace | ++** | + | ++** | − | − |
| CysC | − | trace | + | +++*** | +++** | ++* | trace | trace | + | +++*** | +++** | +++** | trace | +* |

PEC: parietal epithelial cells;
P: podocytes;
MC: mesangial cells;
ND: not detected;
(−) defined as not detectable;
the total intensity score of ISH and IHC staining from 0-20, 20-50, 50-100, and >100 was defined as trace, (+), (++), and (+++).
*$p < 0.05$; $p < 0.01$; *$p < 0.005$, compared to normal control.

As summarized in Table 5, the major site of mRNA expression of the biomarker genes as described and their-encoded proteins in the IgAN patients with UPF was podocytes and parietal epithelial cells in the glomerulus compared to normal controls, although mRNA expression of OPN was also observed in some renal tubules adjacent to the glomerulus. Besides, mRNA expression of BTNL2 in the patients was also observed in inflammatory cells infiltrating around glomerulus as demonstrated by ISH staining. Further, increased urine protein levels of Tmsb4, OPN, cysC and Serpine 2 were detected in these patients, suggesting that these proteins may be used in non-invasive tests for diagnosis or prognosis of the glomerular disorder.

In conclusion, we applied LCM-isolated glomerular sections from renal tissues of a Prg-IgAN model to perform a transcriptional profiling of glomeruli in the animal model. Further, in both the animal model and IgAN patients with UPF, we demonstrated enhanced glomerular expression of Tmsb4, Serpine2, OPN, BTNL2, S100A8, CysC and their encoded proteins. Specifically and importantly, we proved enhanced urinary protein expression of Tmsb4, Serpine2, OPN, and CysC in IgAN patients with UPF, which is helpful in developing diagnostic and prognostic biomarkers for IgAN in a non-invasive approach (in urine samples).

We claim:

1. A method for diagnosing IgA nephropathy in a subject, comprising analyzing urine from the subject for the expression level of serine or cysteine proteinase inhibitor clade E member 2 (Serpine2) polypeptide, wherein the expression level of Serpine2 polypeptide in said urine from said subject that is increased relative to the expression level of Serpine2 polypeptide in urine from a control indicates that the subject is afflicted with IgA nephropathy.

2. The method of claim 1, wherein the urine is obtained in a non-invasive way.

3. The method of claim 1, wherein the expression level of the Serpine2 polypeptide is measured by immunohistochemistry, western blotting, or enzyme-linked immunosorbent assay (ELISA).

4. A method for diagnosing IgA nephropathy in a subject, comprising analyzing urine or renal tissue from the subject for the expression level of serine or cysteine proteinase inhibitor clade E member 2 (Serpine2) gene, wherein the expression level of Serpine2 gene in said urine or renal tissue from said subject that is increased relative to the expression level of Serpine2 gene in urine or renal tissue from a control indicates that the subject is afflicted with IgA nephropathy and wherein the expression level is determined by measuring an mRNA level of Serpine2.

5. The method of claim 4, wherein the mRNA levels are measured by reverse transcriptase polymerase chain reaction (RT-PCR) or in situ hybridization (ISH).

* * * * *